US006261360B1

(12) United States Patent
Dry

(10) Patent No.: US 6,261,360 B1
(45) Date of Patent: *Jul. 17, 2001

(54) SELF-REPAIRING, REINFORCED MATRIX MATERIALS

(76) Inventor: Carolyn M. Dry, 1505 Park Haven Dr., Champaign, IL (US) 61821

( * ) Notice: Subject to any disclaimer, the term of this patent is extended or adjusted under 35 U.S.C. 154(b) by 0 days.

This patent is subject to a terminal disclaimer.

(21) Appl. No.: 09/447,894

(22) Filed: Nov. 23, 1999

Related U.S. Application Data

(63) Continuation of application No. 08/918,630, filed on Aug. 22, 1997, now Pat. No. 5,989,334, which is a continuation of application No. 08/537,228, filed on Sep. 29, 1995, now Pat. No. 5,660,624, which is a continuation of application No. 08/189,665, filed on Feb. 1, 1994, now abandoned, which is a continuation-in-part of application No. 08/174,751, filed on Dec. 29, 1993, now Pat. No. 5,575,841, which is a continuation of application No. 07/540,191, filed on Jun. 19, 1990, now abandoned.

(51) Int. Cl.$^7$ ............................ C04B 14/38; C04B 16/06; C04B 14/42; B32B 3/20; C08J 9/32

(52) U.S. Cl. ......................... 106/677; 106/711; 106/724; 106/729; 106/823; 106/802; 106/805; 106/676; 106/819; 501/95.1; 75/300; 428/320.2; 428/321.1; 428/321.5; 523/218; 523/219

(58) Field of Search ................................. 106/677, 676, 106/711, 724, 729, 819, 823, 802, 805; 501/95.1; 75/300; 428/320.2, 321.1, 321.5, 364, 375; 523/218, 219

(56) References Cited

U.S. PATENT DOCUMENTS

| | | |
|---|---|---|
| 3,179,600 | 4/1965 | Brockett . |
| 3,475,188 | 10/1969 | Woodhouse et al. . |
| 3,505,244 | 4/1970 | Cessna . |
| 3,704,264 | 11/1972 | German . |
| 4,109,033 | 8/1978 | Blankenhorn . |
| 4,587,279 | 5/1986 | Salyer et al. . |
| 4,961,790 | 10/1990 | Smith et al. . |
| 5,232,769 | 8/1993 | Yamato et al. . |
| 5,561,173 | 10/1996 | Dry . |
| 5,575,841 | 11/1996 | Dry . |
| 5,660,624 | 8/1997 | Dry . |
| 5,803,963 | 9/1998 | Dry . |
| 5,989,334 | 11/1999 | Dry . |

FOREIGN PATENT DOCUMENTS

| | | |
|---|---|---|
| 0107086 | 5/1984 | (EP) . |
| 0005529 | 1/1983 | (JP) . |
| 0013227 | 1/1983 | (JP) . |
| 0013229 | 1/1983 | (JP) . |
| 0108262 | 4/1989 | (JP) . |
| 0113436 | 5/1989 | (JP) . |
| 0145383 | 6/1990 | (JP) . |

OTHER PUBLICATIONS

Dry, Carolyn, "Building Materials, Which Evolve and Adapt Over Time—Use of Encapsulation Technology" *Proceedings of the ARCC Research Conference '88*, School of Architecture, University of Illinois, Urbana–Champaign, Illinois, Nov. 13–15, 1988 (no month).

Kroner, W., B. Givoni and C.M. Dry, "Changeable Properties of the Building Envelope—Adaptability to Changing Performance Requirements", *Proceedings of the 3$^{rd}$ International Congress on Building Energy Management*, vol. IV, Lucerne, Switzerland, Sep. 28–Oct. 2, 1987, pp. 117–122.

Dry, C., "Passive Tuneable Fibers and Matrices", *International Journal of Modern Physics B*, vol. 6, Nos. 15 & 16, pp. 2763–2771, World Scientific Publishing Company, Rivers Edge, NJ, 1992 (no month).

Dry, C., "Passive Smart Materials for Sensing and Actuation", *Journal of Intelligent Material Systems and Structures*, vol. 4, No. 3, pp. 415–418, Blacksburg, VA, Jul. 1993.

Dry, C. "Matrix cracking repair and filling using active and passive modes for smart timed release of chemicals from fibers into cement matrices", *Journal of Smart Materials and Structure*, vol. 3, No. 2, pp. 118–123, Jun. 1994.

Dry, C.M., "Smart Building Materials Which Prevent Damage or Repair Themselves", Mat. Res. Soc. Symp. Proc. vol. 276, pp. 311–314, Materials Research Society, 1992 (no month).

Dry, C.M., "Design of Systems for Time Delayed Activated Internal Release of Chemicals in Concrete from Porous Fibers, Aggregates or Prills, to Improve Durability", Doctoral Dissertation, Virgina Polytechnic Institute, Blacksburg, VA, Jan., 1991.

Time Magazine, Apr. 8, 1966, "Capsule Solution for Countless Problems", p. 70.

Kosmatka et al. "Design & Control of Concrete Mixtures", Thirteenth Edition, 1988 PCA, pp. 64–65 (no month).

(List continued on next page.)

Primary Examiner—Michael Marcheschi
(74) Attorney, Agent, or Firm—John W. Cornell

(57) ABSTRACT

Self-repairing, fiber reinforced matrix materials include a matrix material including inorganic as well as organic matrices. Disposed within the matrix are hollow fibers having a selectively releasable modifying agent contained therein. The hollow fibers may be inorganic or organic and of any desired length, wall thickness or cross-sectional configuration. The modifying agent is selected from materials capable of beneficially modifying the matrix fiber composite after curing. The modifying agents are selectively released into the surrounding matrix in use in response to a predetermined stimulus be it internal or externally applied. The hollow fibers may be closed off or even coated to provide a way to keep the modifying agent in the fibers until the appropriate time for selective release occurs. Self-repair, smart fiber matrix composite materials capable of repairing microcracks, releasing corrosion inhibitors or permeability modifiers are described as preferred embodiments in concrete and polymer based shaped articles.

144 Claims, 15 Drawing Sheets

OTHER PUBLICATIONS

Dry, C. M., "Building Materials Which Evolve and Adapt Over Time", Jun. 19, 1989.

Vigo, T. L. and Frost, C. M., "Temperature–Adaptable Hollow Fibers Containing Polyethylene Glycols" Apr., 1973 (no month).

Geishauser, C. B. and Cady, P. D., "A Study of the Heat Treating Cycle for Internally Sealed Concrete Containing Montan–Paraffin Wax Beads", 1977. (no month).

Ivan Amato, Science, Jan. 17, 1992, vol. 255, pp. 284–286, Research News, Animating the Material World.

C. Dry and N.R. Sottos, Passive smart self–repair in polymer matrix composite materials, School of Architecture, University of Illinois at Urbana–Champaign, Department of Theoretical and Applied Mechanics. Feb., 1993.

Carolyn Dry, Passive Tuneable Fibers and Matrices, International Journal of Modern Physics B, vol. 6, Nos. 15 & 16, pp. 2763–2771, World Scientific Publishing Company. 1992. (being re–submitted because previous copy was incomplete). (no month).

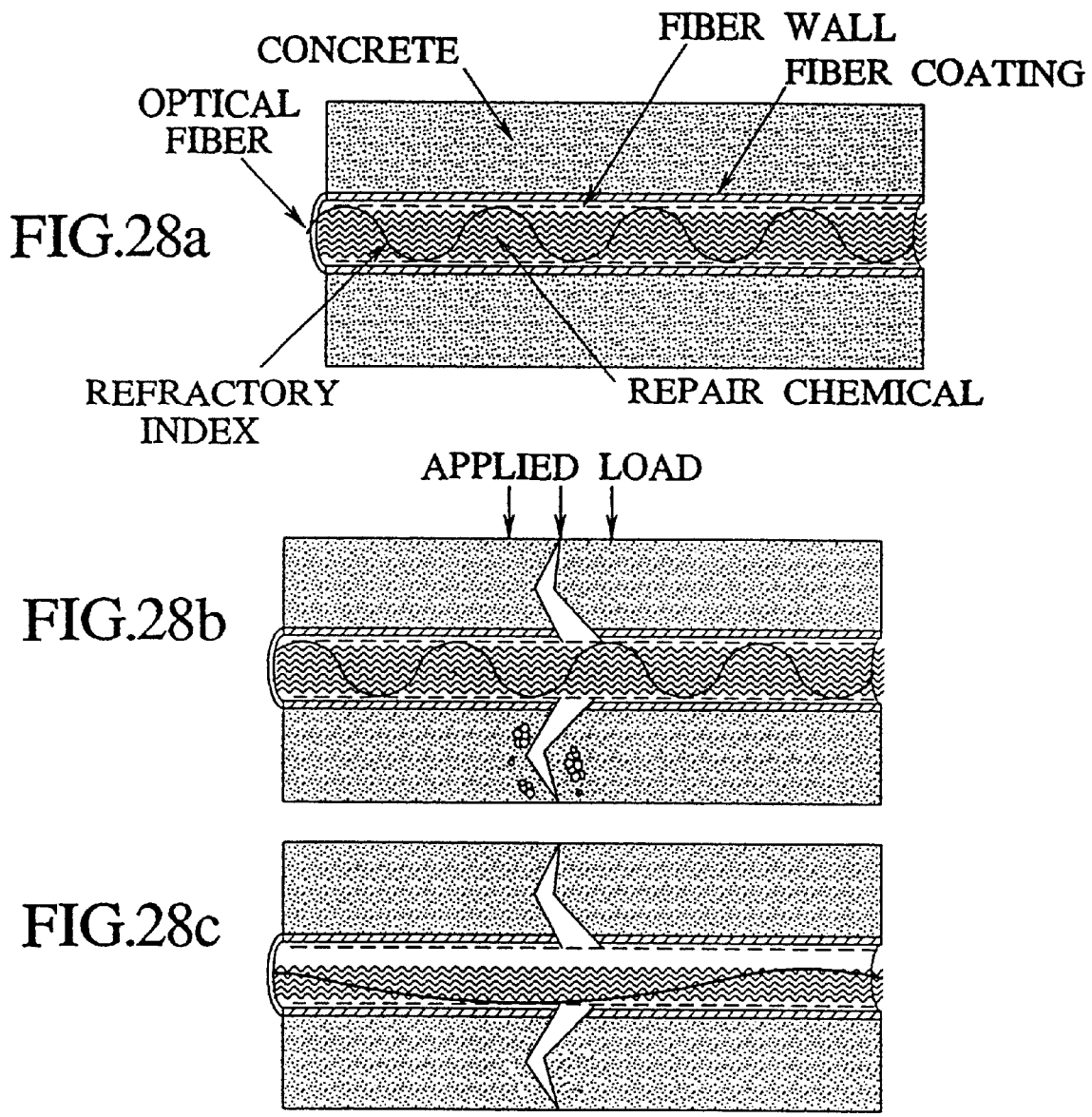

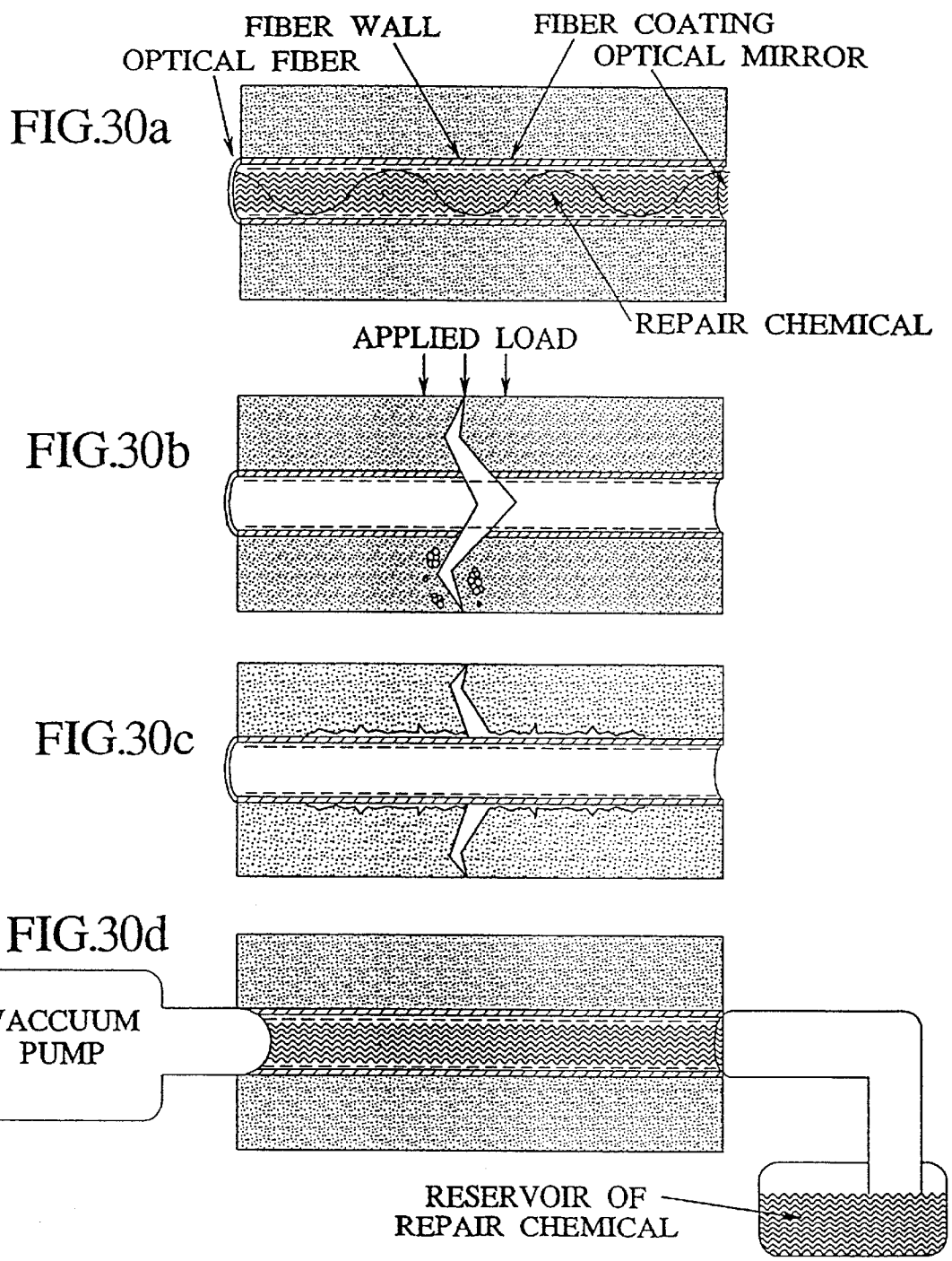

SELF-REPAIRING, REINFORCED MATRIX MATERIALS

CROSS-REFERENCE TO RELATED APPLICATIONS

This application is a Continuation of my prior application Ser. No. 08/918,630, filed Aug. 22, 1997, now U.S. Pat. No. 5,989,334, which is a Continuation of Ser. No. 08/537,228, filed Sep. 29, 1995, now U.S. Pat. No. 5,660,624, which is in turn a Continuation of Ser. No. 08/189,665, filed Feb. 1, 1994; now abandoned, which is a Continuation-In-Part of Ser. No. 08/174,751, filed Dec. 29, 1993, now U.S. Pat. No. 5,575,841, which is in turn a Continuation of Ser. No. 07/540,191; filed Jun. 19, 1990, now abandoned.

BACKGROUND OF THE INVENTION

The present invention generally relates to matrix materials for use in a wide variety of end use fields and applications. More particularly, the invention relates to new and improved self-repairing, settable or curable matrix material systems containing so-called smart-release fiber reinforcements, alone or in combination with other reinforcement. My prior parent application, Ser. No. 540,191, filed Jun. 19, 1990, describes the new and improved inorganic and organic matrix composites employing concrete matrix systems and asphalt matrix systems as illustrative embodiments. That prior application describes smart-release hollow fiber additives in settable construction materials and thermoplastic matrices, such as asphalt. This application is being filed to describe other embodiments of the smart-release matrix composite materials generally described in my earlier application and to provide additional examples of end use applications to which these new and improved compositions, articles and methods may be specially adapted and used.

Cement is a fine, gray powder consisting of alumina, lime, silica and iron oxide which sets to a hard material after mixture with water. Cement, along with sand and stone aggregate, make up concrete, the most widely used building material in the world. Steel reinforcing bars (rebars) are commonly added to the interior of concrete for additional strength.

There are many reasons for the popularity of concrete. It is relatively inexpensive, capable of taking on the shape of a mold, has exceptionally high compression strength and is very durable when not exposed to repeated freeze-thaw cycles. However, as a building or construction material, concrete, whether it is reinforced or not, is not without some shortcomings. One major drawback of concrete is that it is relatively low in tensile strength. In other words, it has little ability to bend. Concrete also has little impact resistance and is frequently brittle. A third major drawback is that its durability is significantly reduced when it is used in applications which require it to be exposed to repeated freeze-thaw cycles in the presence of water. Concrete is relatively porous and water is able to permeate the material. Freezing and thawing with the accompanying expansion and contraction of the water, forms cracks in the concrete. Furthermore, if salt is also present in the environment, it dissolves in the water and permeates into the concrete where it is capable of inducing corrosion in any of the rebars or other metallic reinforcements present.

Various techniques have been suggested in the past for overcoming these drawbacks. The addition of fibers to concrete has improved its tensile strength but has decreased its compression strength. Providing exterior coatings on the outer surfaces of the concrete has reduced water permeation, but it is a time-consuming additional step and has little, if any, effect on the lasting strength of the concrete. The addition of modifying agents as freely-mixed additives into a concrete mixture before setting has also been tried. These efforts have met with generally unsatisfactory results. Attempts to add modifying agents in the form of micronodules or prills have also been tried. Frequently, the prills are designed to be heat melted to cause release of the modifying agent into the matrix after setting of the materials. These designs require the application of heat to release the beneficial additive into the matrix after cure. Moreover, the melted, permeated agents leave behind voids in the concrete which weakens the overall structure under load. Accordingly, a demand still exists for an improved concrete matrix material having greater tensile strength, greater durability and comparable or improved compression strength.

In addition to cementitious building materials, the use of polymer composites as structural materials has grown tremendously in recent years. Polymer composite materials have advantages over steel or concrete including good durability, vibration damping, energy absorption, electromagnetic transparency, toughness, control of stiffness, high stiffness to weight ratios, lower overall weight and lower transportation cost. These polymer matrix materials comprise a continuous polymer phase with a fiber reinforcement therein. Some polymer composite materials are three times stronger than steel and five times lighter. They have heretofore been generally more expensive but their use may, in the long term, be economical because of their greatly reduced life cycle costs. Europeans have made bridges completely of specialty polymer matrix composite materials. The polymer composite materials may be used as rebars, tensioning cables, in bonded sheets, wraps, decks, supports, beams or as the primary structures for bridges, decks or buildings. Structures made from polymer matrix materials are specially effective in aggressive environments or are well adapted for building structures where electromagnetic transparency may be needed for highways, radar installations and hospitals.

As used herein, matrix composite materials may refer to generally any continuous matrix phase whether it comprises a settable construction material such as cementitious materials or a thermoplastic material such as asphalt materials, as well as, other synthetic or natural high polymer materials, ceramics, metals and other alloy materials. The matrix composite materials include various fiber reinforcements therein distributed throughout the matrix or placed at desired locations within the continuous phase. The matrix composite materials may be fabricated as large building structures and load bearing shaped articles, or they may be molded or machined as small parts for specialty uses. For example, the matrix material may comprise a thin sheet or web of material in the form of a foil, wrap, tape, patch or in strip form. As presently used in this specification, the term matrix composite material does not necessarily refer to large civil engineering structures such as highways and bridges.

In connection with the polymer and/or metal or ceramic matrix composite materials, as well as, in the settable building materials such as concrete materials, special problems cause structures made from these materials to become aged or damaged in use. More particularly, special structural defects arise in use including microcracking, fiber debonding, matrix delamination, fiber breakage, and fiber corrosion, to name but a few. Any one of these microscopic and macroscopic phenomena may lead to failures which alter the strength, stiffness, dimensional stability and life span of the materials. Microcracks, for example, may lead to major structural damage and environmental degradation. The microcracks may grow into larger cracks with time and cause overall material fatigue so that the material deteriorates in long-term use.

Advanced matrix composites used in structural applications are susceptible to damage on both the macro- and microscopic levels. Typical macroscopic damage to composite laminates involves delaminations and destruction of the material due to impact. On the micrographic scale, damage usually involves matrix microcracking and/or debonding at the fiber/matrix interface. Internal damage such as matrix microcracking alters the mechanical properties of shaped articles made therefrom such as strength, stiffness and dimensional stability depending on the material type and the laminate structure. Thermal, electrical and acoustical properties such as conductance, resistance and attenuation have also been shown to change as matrix cracks initiate. Microcracks act as sites for environmental degradation as well as for nucleation of microcracks. Thus, microcracks can ultimately lead to overall material degradation and reduced performance.

Moreover, prior studies have shown that microcracks cause both fiber and matrix dominated properties of the overall composite to be effected. Fiber dominated properties such as tensile strength and fatigue life may be reduced due to redistribution of loads caused by matrix damages. Matrix dominated properties on the other hand such as compressive residual strength may also be influenced by the amount of matrix damage. The impact responses of toughened polymer matrix composites have been studied and it has been shown that matrix cracking precedes delamination which, in turn, precedes fiber fracture. Tough matrices which can reduce or prevent matrix cracking tend to delay the onset of delamination which results in an improved strength composite and longer lasting composite material.

Repair of damages is a major problem when these matrix composite materials are employed in large-scale construction or advanced structures. Macroscale damage due to delamination, microcracking or impacts may be visually detected and can be repaired in the field by hand. Microscale damage occurring within the matrix is likely to go undetected and the damage which results from this type of breakdown may be difficult to detect and very difficult to repair.

In order to overcome the shortcomings of the prior art construction and polymer matrix composite materials, it is an object of the present invention to provide new and improved smart structural composite materials having a self-healing capability whenever and wherever cracks are generated.

It is another object of the present invention to provide new and improved composite materials including self-repairing reinforcing fibers capable of releasing chemical agents into the local microscopic domains of the matrix to repair matrix microcracks and rebond damaged interfaces between fibers and matrices.

It is a further object of the present invention to provide a new and improved structural material.

It is another object of the present invention to provide a new and improved cementitious material.

It is still a further object of the present invention to provide a new and improved cementitious or other construction composite material having greater durability and greater tensile strength.

It is still another object of the present invention to provide a new and improved matrix composite materials containing smart self-repairing fiber reinforcement containing repair chemicals therein which may be released by the smart fibers as needed in response to an external stimulus, and optionally which may be refilled with additional repair chemicals as needed in the field.

SUMMARY OF THE INVENTION

In accordance with these and other objects, the present invention provides new and improved shaped articles comprising:

a shaped or cured matrix material having a plurality of hollow fibers dispersed therein, said hollow fibers having a selectively releasable modifying agent contained therein, means for maintaining the modifying agent within the fibers until selectively released and means for permitting selective release of the modifying agent from the hollow fibers into the matrix material in response to at least one predetermined external stimulus. In accordance with this invention the shaped articles are matrix composite materials of varying size and end use applications. The cured matrix materials have within them smart fibers capable of delivering repair chemicals into the matrix wherever and whenever they are needed.

The present invention also provides a new and improved method for providing shaped articles having long-term durability and environmental degradation resistance comprising the steps of providing a curable matrix composition, distributing a plurality of hollow fibers therein in desired manner so that the hollow fibers are disposed within the matrix material in a desired predetermined distribution. The hollow fibers are filled with a selectively releasable modifying agent therein which is not released during the mixing or distributing step. The fibers are structured so that the modifying agents stay within the interior spaces or cavities of the fibers within the matrix until the matrix is cured or set. After curing, the modifying agents are selectively released from the fibers by application or action of at least one predetermined external stimulus.

In a preferred embodiment, the method of providing a improved durability shaped article comprises providing a cured matrix material containing smart self-repair fibers reinforcement therein.

The principles of the present invention are applicable to space age polymer, metal and/or ceramic structural matrix composite materials as well as more conventional cementitious settable or curable building or construction materials.

Other objects and advantages will become apparent from the following Detailed Description of the Preferred Embodiments, taken in conjunction with the Drawings in which:

BRIEF DESCRIPTION OF THE DRAWINGS

FIGS. 1a–1f are schematic views of the new and improved self-repairing fiber reinforced matrix composite material in accordance with the present invention, illustrating a smart matrix repair sequence of load-induced cracking, modifying chemical release and subsequent rebonding and repair of the fiber and matrix and wherein FIG. 1a shows the smart fiber reinforced matrix composite prior to loading, FIG. 1b shows a lateral loading of the composite; FIG. 1c shows a crack formed through the smart fiber and matrix in response to the load, FIG. 1d shows release of modifying agent from the cracked smart fiber, FIG. 1e shows that the repair adhesive modifying agent flows to fill the cracks in the fiber and matrix, and FIG. 1f shows setting of the adhesive to rebond fiber to fiber, fiber to matrix and matrix to matrix to structurally repair the load induced cracking;

FIG. 23c is a schematic view of the alternate embodiment similar to FIGS. 23a and 23b wherein a separate water barrier layer is employed as a first line of defense in combination with the hollow smart fibers in accordance with this invention, which in turn contains water binding hydroscopic chemical agent such as XYPEX, or the like;

FIGS. 28a–28c illustrate schematically optical fiber/smart fiber reinforcements for concrete matrices and demonstrate that the release, repair mechanisms may change the refracturing index transmission properties of the fluid so that the repair fiber itself may indicate the fact of rupturing repair and may also indicate the volume of the cracks filled;

FIGS. 30a–30d illustrate a schematic view of an alternate embodiment wherein a smart fiber reinforcement comprises an optical fiber filled with a repair chemical employing mirrors as shown in FIG. 30a to assist in locating where a crack damage has occurred as shown in FIG. 30b and showing repair and rebonding of the repair chemical into the vicinity of the crack as shown in FIG. 30c and further showing in FIG. 30d the optional replenishment of the repair chemical from an outside source using a vacuum pump.

DETAILED DESCRIPTION OF THE PREFERRED EMBODIMENTS

Figure 1A:
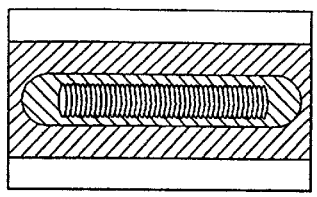

In accordance with the present invention, new and improved shaped articles comprise curable, settable, crosslinkable and/or hardenable matrix materials. The matrix material comprises a continuous phase and is a material that may be shaped to form a three-dimensional shaped article adapted for a particular use. Matrix materials can include any curable, settable or hardenable materials used in construction, building, roofing, roadway, aircraft, automotive, marine, appliances, transportation and/or biomedical fields for making shaped articles. Typically these materials will be moldable or castable to form shaped objects or may be laminated or assembled into finished products. The matrix materials may be inorganic or organic in nature and may include by way of illustration: cement, concrete, sintered fly ash or bottom ash/phosphoric acid mixtures, ceramics including, for example, silicon oxide, titanium oxide, silicon nitrite, graphite, carbon, and metals such as aluminum, steel or other metal alloys, asphalt, thermoplastic polymers, thermosetting polymers, thermoplastic elastomers, crosslinkable polymers, curable polymer resin systems and hydroxyapatite. Illustrative thermoplastic polymers include polyolefins, polyesters, polycarbonates, polyacrylates, polyarylates, polyamides, polyimides, polyaramides, polyurethanes, foaming polyurethane compositions and any other thermoplastic polymers used as engineering thermoplastics for making shaped articles. Thermosetting and crosslinkable polymers and curable resin systems may include, for example, one and two part epoxies, phenolformaldehyde resins and other thermosetting and crosslinkable polymers. Thermoplastic elastomers can include rubbery polymers and copolymers including, for example without limitation, styrene-butadiene, rubber, neoprene, SEBS, NBR, and, EPDM rubbers and the like. Visco-elastic materials and various latex materials may also be used. The matrix materials may also comprise sinterable ceramic materials including hydroxyapatites, as well as, other ceramic materials such as silicas, titanium, carbides, oxides and alumina. The matrix materials may also comprise metal matrices including aluminum, iron, lead, copper, steel, bronze, phosphor bronze, brass and other alloys, as well as biomimetic systems like bone matrices formed of various calcium salts, as well as other organic and inorganic materials.

The matrix materials in accordance with this invention are processable to form shaped articles by molding, casting, sintering, laminating, machining, extruding, or other material fabrication method useful with the matrix material selected. The size and configuration of the finished shaped article produced is essentially unlimited including various small machined parts to very large engineering construction panels for use in building roadway and transportation applications. The matrix materials may be cured by means of catalysts, crosslinkers, radiation, heat, moisture, cooling or by any means used in this art for setting up, hardening, rigidifying, curing, setting or shaping these matrix materials to form shaped articles or objects.

The new and improved shaped articles of this invention additionally comprise hollow fibers having interior spaces therein for containing selectively releasable modifying agents. The hollow fiber materials may include inorganic fibers or organic fibers. Illustrative inorganic fibers include, without limitation: fiberglass fibers, cement fibers, asphalt fibers, hydroxyapatite fibers, glass fibers, ceramic fibers, metal fibers, and the like. Illustrative organic fibers that may be used as the hollow fiber component may include, without limitation: polyolefin fibers, polyester fibers, polyamide fibers, polyaramide fibers, polyimide fibers, carbon fibers, graphite fibers, cellulose fibers, nitrocellulose fibers, hydrocarbon fibers, GORETEX® fibers, KEVLAR® fibers, and the like, to name but a few. Porous polypropyline fibers are a preferred hollow fiber. The hollow fibers may be elastomeric.

The fibers may be bundled, woven or loose. They may be held or engaged together with flexible web materials. They may comprise twisted pairs and additionally may include concentric structures of one or more fibers. The sidewalls of the fibers are typically rupturable or porous to permit the discharge or exiting of the modifying agent into the surrounding cured composite matrix material. The fibers may come in different shapes, volumes, and wall thicknesses. They may be generally notched, have periodic enlargements or bulges, V-shaped, double or multiple lumens, U-shaped, or they may comprise combinations of one or more different types of fibers. For example, double walled fibers are particularly useful for two-part modifying compositions such as epoxies. Doubled fibers including a metallic inside fiber and a glass outer sheath fiber are useful where bending of the metal fiber assists in breaking the glass carrier fiber. Additionally, assembled structures of polypropylene hollow porous fibers disposed inside a glass outer fiber might be used to permit a first break and release of modifying material to occur with the glass fiber and thereafter a secondary break and release of the polypropylene fiber at a later date to provide a specially long-term profile modification to the shaped matrix composites. The smart-release fibers may also be paired or include other specialty fibers such as piezoelectric fibers or optical sensor fibers for providing special monitoring, metering and diagnostic capabilities. Some of these specialty composites will be more particularly described hereinafter. The fibers may also be woven together into a web so that they may be wrapped as an organized bundle around rebars or the like. Although fiber materials are preferred, other container-like smart release structures or vessels may be provided for special end uses. For example, in relatively large structural parts it may be useful to add the repair chemicals in large flat balloons or bags layered or laid up within the matrix or layers of matrix. It should be apparent to those skilled in this art that for certain end uses, small release vessels having a shape somewhat different from hollow fibers for performing the same smart release functions may be employed. In addition, the fibers may be relatively small, chopped or comminuted fibers having diameters of less than about 100 microns. The fibers and matrices may be readily used in usual shaping processes such as in an injection molding operations or the like.

In accordance with this invention, the hollow fibers include certain internal modifying agents which are selectively releasable from the fibers in response to the application of certain predetermined external stimuli. The modifying agents include agents which will modify the performance characteristics of the cured shaped article matrix materials in use. By way of illustration, the modifying agent may include polymerizable monomers such as methyl methacrylates, styrene or other polymerizable starting materials. They may additionally include two part epoxies wherein an epoxy precursor material is disposed in one fiber or in one lumen of a double lumen fiber and the amine or other cross-linking agent is disposed in an adjacent fiber or in the other lumen of the double lumen fiber. Other curable polymerizable monomers may also be employed.

Another modifying agent which may be used herein includes a sealant used to prevent water permeability and ingress or egress of water or other liquid materials to and from the cured matrix composite. Illustrative examples for cement may include oily sealants to prevent ingress of water such as linseed oil or other known sealant materials.

Another important modifying agent for both cementitious and polymer matrices include adhesives which cure in situ to repair microcracks within the matrix in use. Illustrative adhesives include one- and two-part adhesives, one- and two-part epoxy adhesives, cyanoacrylate adhesives, Elmer's glue and others known to those skilled in the art. The adhesives may bond matrix to matrix, fiber to fiber, as well as fiber to matrix.

Certain water barriers are particularly useful modifying agents for cementitious matrices. These may include special ZYPEX® brand sodium silicate additives as well as siloxane and silica additives known as SALT GUARD® and the like.

Another modifying agent useful in the shaped articles of this invention includes anticorrosion agents such as calcium nitrite. These are particularly useful in cementitious matrices employing rebar reinforcements or steel mesh reinforcements.

Another example of a modifying agent which may be disposed in the interior of the hollow fibers for use herein includes antifreeze material such as polypropylene glycol.

Fiber protectors may also be used as the modifying agents which can be materials which protect the fibers themselves within the matrix material. An example of this includes pH modifiers for protecting fiberglass in highly alkaline environments.

Still another class of modifying agents particularly useful in polymer matrices are solvents which permits solvent action to actually repair microcracking damage locally at a cracking site or possibly to dissolve the matrix or fibers or both to permit them to re-form at a later time.

In addition to solvents, other curable monomers and co-monomers may also serve this repair function. pH modification agents may also be used as the modifying agents, either alkali or acidic agents, which may be placed in the interior of the fibers only to be released by an appropriate pH changes in the matrix. Other additives may include flame retardant agents. Visco-elastic polymers may also be used as modifiers.

Modifying agents for use herein may comprise rheological or electrorheological fluids.

In accordance with this invention, means are provided for maintaining the modifying agent within the hollow fibers. The modifying agents may be physically trapped by, for example, drawing liquid additives into the interior of the fibers and retaining them therein by capillary action or by closing off the ends of the fibers. For brittle fibers, sealing of the ends by heat or pressure may be one method for maintaining the modifying agents therein. Moreover, specialty coatings may be used, which will selectively degrade upon the occurrence of a particular external stimulus. Illustrative examples might include heat sensitive coatings, pH sensitive coatings, ion sensitive coatings, and the like. These coatings are effective to close off the pores of the hollow fiber walls or the ends of the fibers to prevent premature leakage of the modifying agent until the intended time. Illustrative coatings may include waxes, low molecular weight hydrocarbon oils and coating polymers to name but a few. More particularly, the coatings may include chemically sensitive coatings, electrically sensitive coatings and/or radiation sensitive coatings. Chemically sensitive coatings may include moisture sensitive coatings, pH sensitive coatings, ion sensitive coatings or solvent sensitive coatings. Electrically sensitive coatings may include current sensitive coatings or voltage sensitive coatings. Radiation sensitive coatings may include light sensitive coatings, temperature sensitive coatings or radioactivity sensitive coatings.

In accordance with the present invention, means for permitting selective release of the modifying agent in response to the external stimulus may be provided. Illustrative examples include the selectively removable or dissolvable coatings which give way to permit leakage of the modifying agent in response to, for example, stimuli such as heating, cooling, loading, impacting, cracking, water infusion, chloride infusion, alkalinity changes, acidity changes, acoustic excitation, low frequency wave excitations, hydrostatic pressure, rolling pressure, light sensitivity or laser excitation, or the like. Electrical currents, voltages, electrorheological excitation, radiation, or other energetic stimuli may also be employed or effective to permit or cause selective release of the modifying agent or agents from the fibers.

In accordance with this invention, the selective release of the modifier occurs in the matrix when and where it is required and may lead to improved toughness, strength, ductility, brittleness, permeability, fire retardancy, stiffness, dimensional stability, modulus of elasticity, fatigue, impact resistance, and other improved properties. Specially important in accordance with this invention is the ability to repair small microcracks forming in the reinforced matrix composites. The selective release of the modifying agent may be chosen to be effective to rebond the fibers to the matrix, to repair the fibers themselves, to improve or restore the matrix to fiber interface, to repair delaminations, and to repair microcracks in the matrix itself which may repair or overcome cracking or corrosion induced dimensional weaknesses and ultimately reduced durability for the shaped articles.

In accordance with an embodiment, the shaped articles in accordance with the invention include a plurality of modifying agent-filled hollow fibers present in an amount of less than about 10 volume percent of the matrix material.

Selective release of modifying agent may be provided in several ways. For example, when the hollow fiber is piezoelectric, pressure stimulation causes charging of the fiber which is effective to discharge oppositely changed ions present in the modifying agent out of the fiber. Alternatively, electrical stimulation of a piezoelectric fiber causes the fiber to constrict, thereby squeezing modifying agent out of the fiber. A hollow fiber of a shape memory alloy may respond to temperature change stimulation which causes the fiber to change shape thereby squeezing the modifying agent out of the fiber. Magnetic stimulation causes magnetostrictive hollow fibers to constrict, thereby squeezing modifying agent out of the fiber. In addition electrical stimulation of electrostrictive hollow fibers causes the fiber to constrict, thereby squeezing modifying agent out of the fiber.

As has been mentioned above, the shaped articles in accordance with this invention may be used for a number of applications, both large and small. Large construction applications are particularly preferred, particularly those used in harsh environments or for outdoor use. Illustrative end use applications for the new and improved shaped articles in accordance with this invention include, for example without limitation, structural sandwich panels, exterior applied insulation panels, fire panels, construction building blocks, cements, concretes, fireproof doors, panels, walls, hazardous waste containment vessels, engines, concrete building blocks, roadways, bridges, dams, engines, road surfaces, roofing blocks, roofing shingles, decks for parking garages, and other building structures and columns. Other construction applications might include the use of these shaped, cured, smart-release composites in bridges, post-tensioning cables, road decks, road deck overlays, aircraft body components, including fuselages, wings and tip design, machined parts, helicopter blades as well as the aforementioned roofing structures.

The shaped articles of this invention might also be useful in biomedical applications as bone replacements as prosthetic devices and as biomedical adhesives.

More particularly, shaped articles of this invention may be used to form self-growing structures. In accordance with this aspect of the invention, the goal is to create a ceramic resembling bone which is an organic-inorganic composite created at low temperature due to the presence of organisms. Bone is made up of an oriented matrix which is secreted by bone forming cells referred to as osteoblasts. In natural bone, organic matrices are made up of structural molecules which serve as a scaffolding and which are laid down in very precise, oriented pattern of fibrils into and onto which inorganic crystalline phases form. The formation of the first crystals of inorganic salts of calcium phosphate are often referred to as initiation or nucleation which occurs along nucleation sites which appear at regular intervals along the organic scaffolding, usually collagen laid down by osteoblasts. Once nucleation has occurred, the next major process involves the continuation of crystalline growth from these nucleation sites outward along the fabric of the organic matrix and eventually between the molecules which serve as scaffolding. As crystal growth continues and forms against inorganic matrix, there is a loss of organic components which are designed to reserve space in the matrix forever expanding the inorganic phase.

In accordance with this biological models, the present invention may be employed to provided a self-growing structure something like bone, wherein the hollow pores polymer fibers may release chemicals and act as an organic template on which to form a strong structural bone-like composite. This self-growing structure might be used for structural materials as well as for computer chips or for prosthetic devices. More particularly, just as ligaments or tendons have been used as natural matrices to form bone materials, these polymer tubes or fibers are used in accordance with the present invention to concentrate bone-like substances. The fibers are hollow and have porous walls. In accordance with this invention chemicals are released from the hollow fibers, particularly polymeric materials which are designed to cause targeted release of water in an inorganic matrix to form a structural network of calcium phosphate materials. Instead of using collagen gels to form a backbone network, in accordance with this invention, a matrix material including inorganic cementitious salts and a first polymer reactant may be provided which includes hollow fiber materials including a condensable or cross-linkable moiety reactive with polymer. Under appropriate conditions, release of the co-reactant from the fibers causes a condensation reaction of the matrix polymer in which water is produced. The water byproduct of the condensation reaction is used to hydrate cement to build up a structural backbone along the fiber regions.

In accordance with another aspect of the invention, a hollow porous polymer fiber material may be placed in a calcium phosphate material matrix in which a polymer powder monomer is present. A cross-linking monomer is then released from the fibers into the matrix. The ensuing condensation polymerization reaction releases water, which then hydrates the calcium phosphate materials. Xypex or other cement crystallizing initiator materials may carry the hydration reaction away from the polymer fiber scaffolding within the inorganic matrix. The structural make-up of these materials may be designed to resist stresses by including piezoelectric fibers within the matrix. Lines of force may be generated by prestressing or stressing the piezoelectric polymer fibers along which charged cementitious ions will migrate. This will cause the polymer matrix to rearrange and the composite prestressing forces therefore will generate an appropriate microstructure within the material.

Also in accordance with this aspect of the invention, self-healing may be accomplished by leaving some of the original fibers void or by adding additional fibers designed with specialty repair chemicals for repairing the system. Hollow porous fibers may be used to deliver repair chemicals at a later time if damage such as cracking occurs. Repair chemicals, either present as an adjuvant fiber additive or added to hollow fibers from the outside, may be used to improve the visco-elasticity of the entire component as desired.

In accordance with this invention, materials may be developed for application in self-repairing materials for use in facings, coatings and membranes. In accordance with this aspect of the invention, the new and improved fiber-containing matrix materials may be provided in the form of paints, membranes, roofing materials, or the like, including self-repairing liquids within the fibers. The materials may be provided in the form of wraps for buildings, bridges, roads, or the like, including webs or fabrics of smart fibers disposed within the matrix. Repair chemicals may repair cracks in the wrap itself or also seep into and repair adjacent structures to which the wrap is adhered to improve the overall structural performance over time. Specialty wraps including solar collecting fibers might also be added to the exterior of previously existing outdoor structures.

Another biological or biomedical application for the new and improved shaped articles of this invention might include smart-release bandages, artificial skin materials, poultices, bandaids and the like which include smart fibers which release healing chemicals or healing promoting chemicals by upon movement of the patient or by application of another stimulus, such as for example, a heating pad, or the like. The smart fibers used in these bandage applications might include such release chemicals as oxygen releasing chemicals, moisturizers, aloe vera, antibiotics, anti-inflammatants, analgesics, non-stick agents or the like.

Another illustrative use of the shaped articles of this invention might be polymer matrices including smart fibers therein which may be made to include dissolving chemicals which ultimately assist in de-naturing, degrading or destroying the polymeric structures by depolymerization or chemical reaction to improve recyclability of the polymer material.

The shaped articles of this invention may also be used in various small shaped article applications including aerospace applications, pipe repair, engine pistons, rubber matrices, waterborne paints and coatings, rubber gasket materials and other seals and in woven fabrics. For example, in fabrics the fibers may contain a fabric glue to repair small tears or abrasions of the fabric. Hard self-repairing shaped articles, such as silicon nitride fibers in carbon-alumina matrices for pistons might be used. Metal matrices that may be employed include metals and alloys such as alumina as well as foamed metals. The fibers for these metallic composites may include adhesive materials or corrosion resistant materials to help repair the matrices or other desirable smart release additives.

The new and improved smart fibers of the present may be disposed within large cross-sectional areas or sections of a matrix prior to cure which may thereafter be used to release curing agents from several positions disposed throughout the curable matrix simultaneously to speed up or assist in the curing of large cross-section polymer articles. Similarly, natural fibers such as wheat straws or the like may be added to concrete or adobe matrices to stabilize the composites so that they do not crumble or flow in use.

In a related application, the new and improved smart matrix materials may be used to perform road repair and pothole repair. In connection with this aspect, smart release fiber-containing uncured material may be added to a pothole. An agitation or pressure may be used to release curative agents from the interior of fibers provided in the matrix material to promote adhesion and curing of the pothole repair mass to the substrate road surface. Additional fibers may be provided containing repair adhesives which release in response to tire pressure, to further strengthen and reinforce the pothole patch in use.

Another highway application of the present invention includes the use of smart release fibers to add phosphorescent chemicals to concrete or asphalt matrices. Phosphorescent roads may clearly demarcate the road or highway surface from non-road driving surfaces at night without the need for street lights or other markers or reflectors. The smart matrix materials would permit renewed release of phosphorescent agents into the road surface, as the layers of the road surface are worn away by highway traffic. A continually replenishing supply of chemicals that could absorb sunlight during the day and re-emit it as phosphorescent light in the evening hours would be provided.

In accordance with another aspect of this invention, the shaped articles may include hollow and continuous matrix formed into a shaped article and having hollow fibers therein which permit visual inspection of the structural part in use. The use of hollow, air-filled fibers permits persons to actually look into and see inside the matrix to see cracks near the fibers. These hollow fibers also permit exterior introduction of chemicals to be performed to add chemicals to a previously cured matrix.

Hollow or filled fibers may be provided with dyes or other sensing or sensible materials to identify the presence of structural stresses or weaknesses and also the locations of these stresses in large structural articles. For example, release of dyed materials from fibers may permit the dye to migrate to the surface to indicate a structural compromise or repair need in a highway, bridge, or the like. Specialty dyes such as X-ray sensitive dyes may be added to help diagnose a small microstructural repair problem. More particularly, if the dye is leaked into the matrix in use due to structural damage, periodic diagnostic teams may test with high energy beams shined into the matrix. The interactive dye would signal back after excitation in a detectable manner so that the need for attention or repair would be revealed. Piezoelectric fibers may also be used to evaluate the state of the matrix. Remote sensing of eddy currents or electrical or magnetic fields generated about the fibers in response to pressures or stress may be detected in a matrix in these ways.

Still another application for the shaped articles of this invention can include non-biological but biomimetic materials wherein a polymer matrix containing crystallizable mineral elements such as alumina alkoxide may be provided. A condensation reactive element or ingredient provided inside the smart fibers may be released on application of appropriate external stimulus from the smart fibers within the matrix containing the alumina crystals. The by-product water of the condensation reaction in this case may be used to cause alumina crystals to grow at specified locations within the shaped article.

Another special useful application of the shaped articles in accordance with this invention is as a containment structures for radioactive or chemical waste materials. In accordance with this aspect, fibers provided with chemically sensitive coatings or radiation sensitive coatings may be provided which are adapted to release scavenger compounds when radiation or chemical waste is detected. The compounds will then migrate from the fibers into the matrix to scavenge and render harmless radioactive or chemical materials leaking into the containment vessels to prevent them from being discharged from the containment area into the environment. Alternatively, permeability modifying agents may be released from the coated fibers to boost the impermeability of the containment vessel to water-borne contaminants.

The new and improved shaped articles of this invention may be employed to form self-repairing impact resistance layers in laminated materials and structures. For example, a clear, transparent polymer matrix containing adhesive filled glass fibers may be used as an interlayer between two safety glass or polymer sheets. Impact fracture of a base sheet will cause local release of repair adhesive from the interlayer to control fragmentation and rebond cracked or fractured sections of a laminate.

As has been mentioned above, various means may be provided to force the repair chemicals out of the fibers. Chemicals may be pumped into hollow fibers from the outside or propellant gases may be injected into previously filled fibers to which external access has been provided to force the chemicals out. Other methods to promote repair chemical release may include electrical, magnetic, and chemical means which alter the shape, permeability or coating integrity of the fibers. Shaped memory alloy materials may be used as the fiber or these materials may be used in the fiber to squeeze the fiber and thereby pump the chemicals out. Fibers which change their shape in response to applied light or magnetic forces or fields may also be used to discharge the chemicals as desired.

The smart release shaped articles and materials in accordance with the present invention may be used throughout building structures to provide earthquake proof buildings which can withstand seismic activity with reduced hazard and damage. This is accomplished by preventing flying debris from being created and by supporting building structures in matrices adapted to visco-elastically respond to seismic vibration.

Because the beneficial improvements provided by the new composition, articles and methods of this invention may be useful for broad range of applications, it is difficult to specifically enumerate each of them. The present invention will be further illustrated by several specific end use applications provided to further illustrate the improvements provided by the present invention.

Figure 1B:
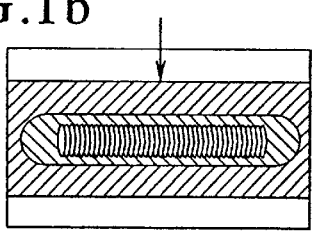
Figure 1C:
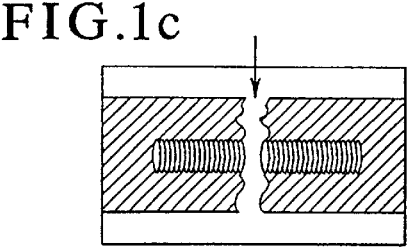
Figure 1D:
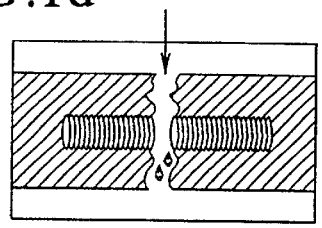
Figure 1E:
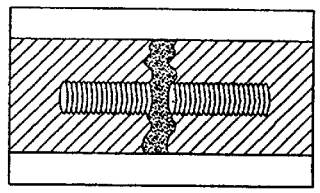
Figure 1F:
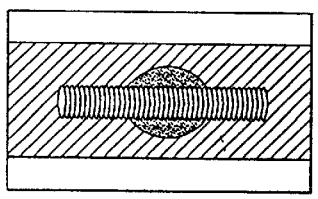
Figure 2A:
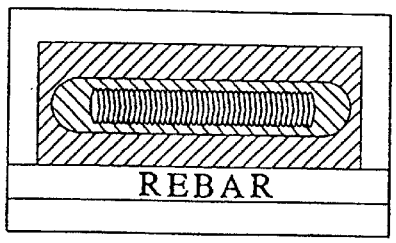
FIGS. 2a–2e are schematic views of the new and improved self-repairing fiber reinforced matrix composite material in accordance with this invention, illustrating a smart matrix repair sequence of salt or pH change penetration into the matrix adjacent a smart fiber wrapped rebar reinforcement causing dissolution of the pH sensitive coating, thereby releasing anticorrosion modifying agents in the domain or vicinity of the rebar to prevent corrosion of the rebar and showing the smart fiber wrapped rebar disposed in a matrix prior to chemical intrusion in FIG. 2a, intrusion of chloride or carbon dioxide into the matrix and causing a pH change in the matrix in FIG. 2b, a breakdown of pH sensitive coating on the smart fibers caused by pH changes in the matrix due to chemical intrusion in FIG. 2c, subsequent release of the anti-corrosion chemical from the smart fibers now rendered porous due to the breakdown of the coating in the viscinity of the rebar in FIG. 2d and illustrating released chemical corrosion protection chemicals around the rebar and preventing corrosion of the rebar in FIG. 2e.
Figure 2B:
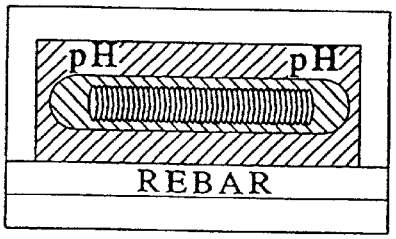
Figure 2C:
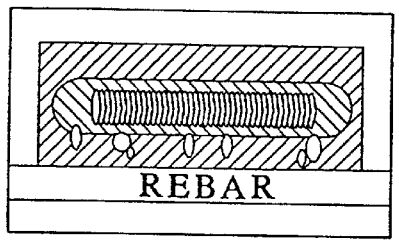
Figure 2D:
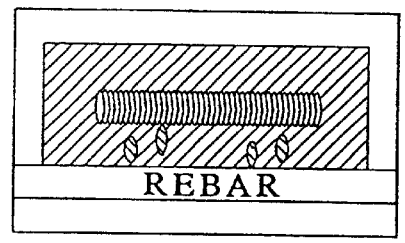
Figure 2E:
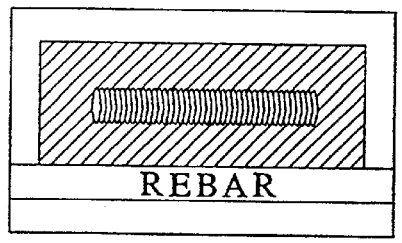

Referring now to FIGS. 1a–1f, the new and improved self-repairing fiber reinforced matrix composite and its operation in the field is shown. As depicted in FIG. 1, a hollow fiber containing an adhesive modifying agent and coated with a thin coating material is dispersed within a settable or curable matrix material which may be either a polymer or cementitious material. As shown in FIG. 1b, a loading applied to a shaped article causes strains within the matrix, which in turn cause the fiber to break and the matrix to crack. This causes the modifying chemical agent disposed within the hollow fiber to be released into the vicinity of the crack in the matrix as shown in FIG. 1b. The modifying agent flows and fills the void as shown in FIG. 1e and eventually cures to rebond the fiber to the matrix and to repair the fiber to itself as shown in FIG. 1f. This schematically illustrates the modified fiber concept of the present invention.

Referring now to FIGS. 2a–2e, a similar smart fiber repair embodiment is depicted wherein the smart hollow fibers contain anticorrosive modifying agent and are coated with fibers which are pH sensitive. These smart fibers are disposed within the matrix adjacent the rebar reinforcement by selectively positioning them adjacent the rebar as the matrix is poured into the concrete mold or the rebar can actually be wrapped with the hollow fibers which have been previously banded together as a web or tape. In accordance with this matrix composite construction, the anticorrosion filled smart fibers are disposed immediately adjacent the rebars. The anticorrosive chemical compounds are not released to protect the rebars unless or until the exchange has occurred in the vicinity of the rebar, either due to chloride iron infiltration or carbon dioxide intrusion. The advance of corrosive chemicals breaks down the pH versus sensitive coating on the smart fiber, releasing the protective anticorrosive agent to protect the rebar from corrosion by the environmental chemicals found in FIGS. 2c–2e.

Figure 3A:
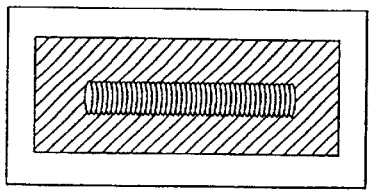
FIGS. 3a–3c are schematic views of the new and improved self-repairing fiber reinforced matrix composite material in accordance with this invention, illustrating a smart matrix repair sequence of freeze/thaw protection including freeze induced release of antifreeze from the fibers to provide an antifreeze-containing matrix to reduce freeze/thaw damage and showing a water-based anti freeze containing smart fiber reinforced matrix in FIG. 3a, a release of antifreeze from the smart fiber into the matrix upon exposure to lower temperatures caused by freezing expansion of water based antifreeze in FIG. 3b and showing a matrix after release containing distributed antifreeze in FIG. 3c to lower freezing temperature of the matrix and reduce freeze thaw damage.
Figure 3B:
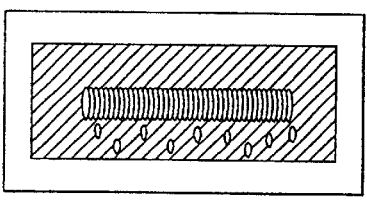
Figure 3C:
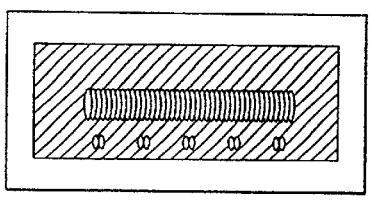

Referring now to FIGS. 3a–3c, the smart fiber matrix is shown in operation in plain and in antifreeze modifying agent disposed within the hollow fibers. A water-based antifreeze expands as it cools to force its way out of the pores in the hollow fiber, thereby dislodging the coating, if present, and permitting the antifreeze to exit into the local environment of the matrix. As shown in FIGS. 3b–3c, the release of the antifreeze into the matrix lowers the freezing temperature of moisture in the materials within the matrix preventing freeze/thaw damage from occurring to the matrix.

Figure 4:
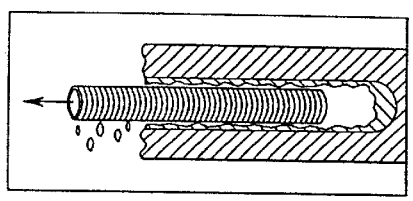
FIG. 4 is a schematic view of the new and improved smart fiber reinforced matrix composite material in accordance with the present invention, illustrating a release, repair mechanism in which the fiber is debonded from the coating and matrix in response to an applied load to release the modifying agent from the uncoated fiber pores.

Referring now to FIG. 4, a debonding of a coated fiber is shown as a mechanism for releasing the modifying agent contained within the smart fiber into adjacent areas of the matrix. This can occur, for example, where there is coating applied to the smart fiber to retain the modifying agent within the fiber interior as a higher affinity for the surrounding matrix in a cured state than to the fiber. Accordingly, debonding of the fiber from its coating allows the pores to become open to permit chemical release.

Figure 5:
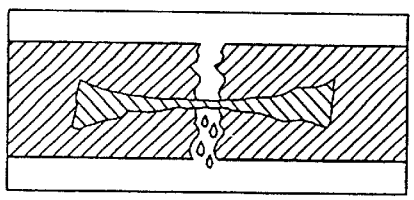
FIG. 5 is a schematic view of a smart fiber reinforced matrix composite material in accordance with this invention, illustrating a release, repair mechanism in which an applied load causes dimensional changes in the fiber promoting release of modifier from the fiber into the matrix.

Referring now to FIG. 5, there is illustrated in the embodiment wherein modifying agent release is caused by torting, twisting or other load changes which cause a dimensional change in the shape of the hollow fiber, which in turn forces the modifying agent out into the surrounding matrix. These torting, twisting or other loads placed on the fiber may cause local debonding of the fiber from its coating, permitting release as shown in FIG. 4 or a mechanical forcing of the contents of the fiber through the pores, which in turn causes dislodgment of the coating may also occur.

Figure 6A:
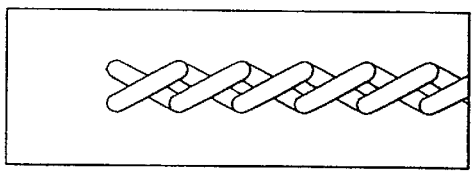
FIGS. 6a and 6b are schematic views of a new and improved matrix composite material in accordance with this invention, illustrating a twisted fiber bundle smart fiber matrix in FIG. 6a and illustrating release and repair from twisted fiber bundles, whereby compressive loading causes unlocking of the twisted fiber bundles to release modifying agent into the adjacent matrix as shown in FIG. 6b.
Figure 6B:
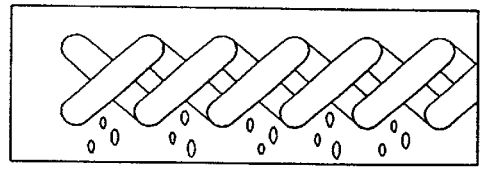

Referring now to FIGS. 6a and 6b, the application of the compressive load on a twisted fiber bundle can cause debonding of the coating from the twisted fibers forcing fluid contained within the hollow spaces of the fiber through the fiber pores and into the surrounding matrix.

Figure 7:
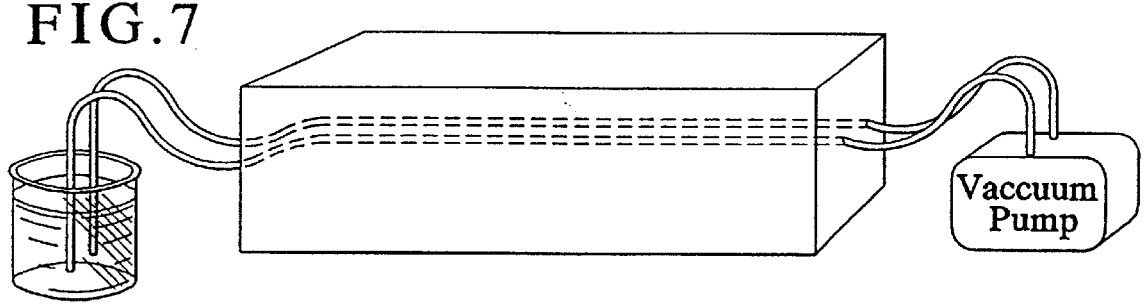
FIG. 7 is a schematic view of a new and improved self-repairing fiber reinforced matrix composite material and system in accordance with the preferred embodiment of this invention, whereby a smart fiber disposed within the matrix may be refilled with replacement modifier as needed by drawing modifier into the fibers using a vacuum pump.

Referring now to FIG. 7, a preferred embodiment of the present invention includes providing the smart hollow fiber reinforcement within a matrix so that end portions of the fiber are accessible from the exterior of the matrix to permit additional modifying agents to be supplied into the fibers of the matrix. As depicted therein, a reservoir of modifying agent may be placed in the fiber and a vacuum pump may be attached to the opposed ends to draw the modifying agent into the fibers to replenish any leaked materials therein.

Figure 8:
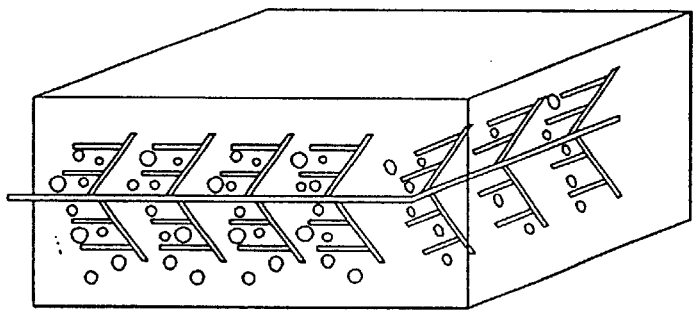
FIG. 8 is a schematic view of a fiber reinforced matrix composite material in accordance with another preferred embodiment of the invention, illustrating a matrix containing a network of interconnected smart fibers into which additional modifying chemicals may be added from the exterior of the matrix in use.

FIG. 8 is an extension of the concept described and schematically illustrated in FIG. 7 wherein a series of hollow smart fiber reinforcements are arranged in a continuous network to permit the additional chemicals to be added from the outside throughout the entire matrix.

Figure 9:
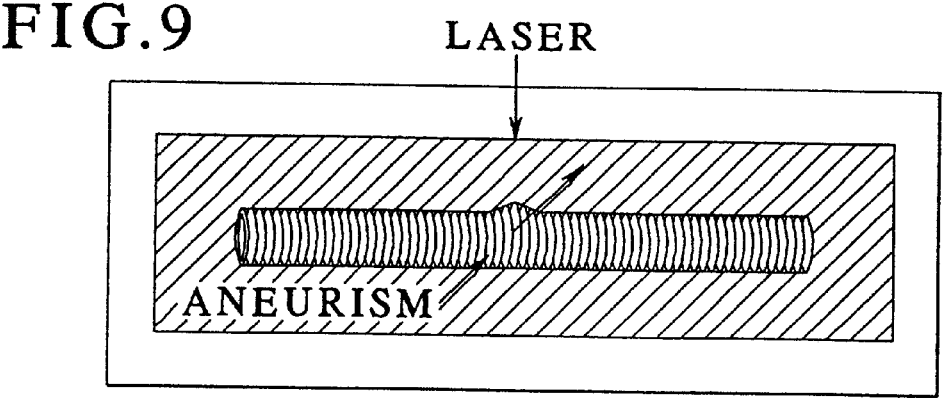
FIG. 9 is a schematic view of the new and improved matrix composite material in accordance with this invention, illustrating a light activated release mechanism employing lasers.

Referring now to FIG. 9, other mechanisms may be employed for dislodging or releasing the modifying agent into the surrounding matrix at a selected time after curing, such as, by example, using laser energy to cause an aneurysm to form in the fiber which permits leakage.

Figure 10:
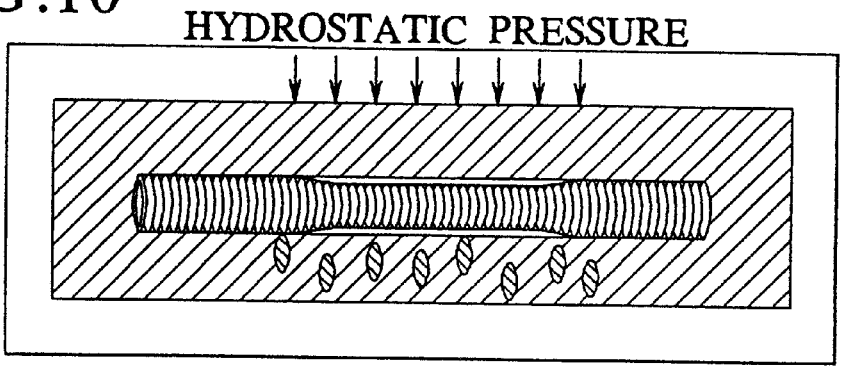
FIG. 10 is a schematic view of the new and improved self-repairing matrix composite material in accordance with this invention, illustrating a hydrostatic pressure induced release and repair mechanism.

Referring to FIG. 10, hydrostatic pressures may also cause the fiber diameter to be locally reduced, causing an exiting of the modifying agent into the surrounding matrix.

Figure 11:
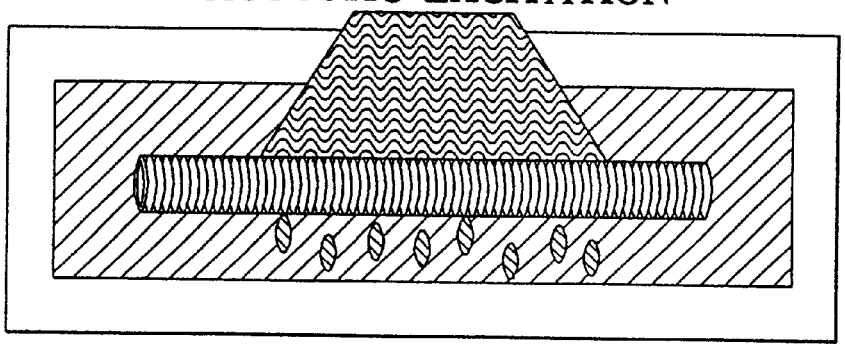
FIG. 11 is a schematic view of a smart fiber reinforced matrix composite material wherein the modifying agents are released from the fibers by acoustic excitation.

FIG. 11 shows an embodiment wherein acoustic excitation is employed as the means for releasing the modifying agent from the fiber.

Figure 12:
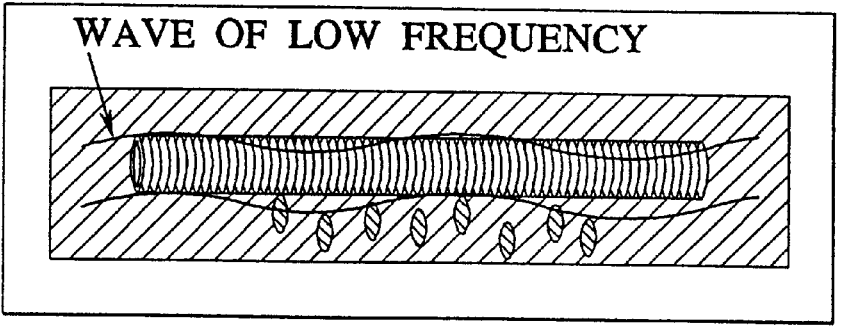
FIG. 12 is a schematic view of a smart fiber reinforced matrix composite material of this invention, illustrating seismic or low frequency wave-induced modifying agent release mechanism.

FIG. 12 is an alternate embodiment wherein waves of low frequency such as seismic waves may pass through the matrix in such a manner as to cause debonding of the fiber from a coating or uncoated fibers may cause the modifying agent to exit from pores disposed within the fiber matrix disposed within the hollow fiber.

Figure 13A:
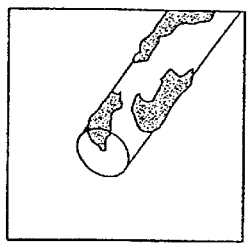
FIGS. 13a and 13e are schematic views comparing the corrosion of rebars possible with conventional cement rebar-reinforced matrices of the prior art, as shown in FIG. 13a, with the corrosion prevention provided by the new and improved smart fiber matrices of this invention, shown in FIG. 13e.
Figure 13B:
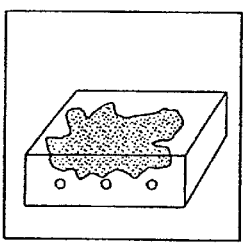
FIGS. 13b and 13f are schematic views illustrating a comparison of the permeability of prior matrices, shown in FIG. 13b, with the impermeability produced by the smart matrix permeability modification agent release mechanisms in accordance with this invention shown in FIG. 13f.
Figure 13C:
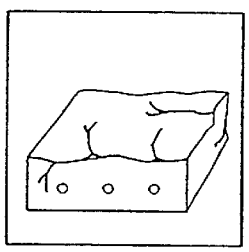
FIGS. 13c and 13g schematically illustrate the internal cracking problems associated with prior art freeze/thaw damage to prior art matrices, shown in FIG. 13c, in comparison with the antifreeze containing smart matrix composite in accordance with this invention shown in FIG. 13g.
Figure 13D:
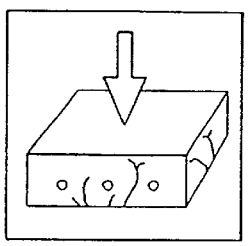
FIGS. 13d and 13h illustrate the load-induced cracking schematically illustrated for a prior art matrix, shown in FIG. 13d, in comparison with the internally released crack prevention and filling smart fiber matrices in accordance with the present invention, shown in FIG. 13h.
Figure 13E:
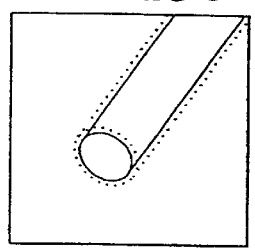

FIGS. 13a through 13h demonstrate in a side-by-side comparison the ability of the smart fiber reinforced matrix composite materials prepared in accordance with this invention to prevent environmental distress and aging frequently encountered by prior art composite materials. A comparison of FIGS. 13a and 13e shows that the modifying agent in FIG. 13e is an entire corrosion agent to prevent corrosion of the rebars and in that case calcium nitrite is preferred.

Figure 13F:
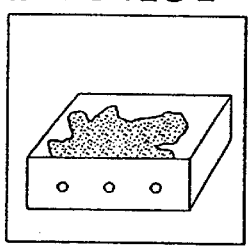
Figure 13G:
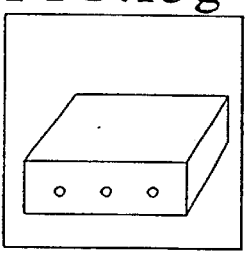
Figure 13H:
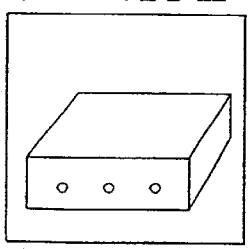
Figure 14:
FIG. 14 is a schematic view of a new and improved smart fiber having a notched wall configuration.
Figure 15:
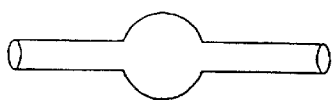
FIG. 15 is a schematic view of a new and improved smart fiber having a bulging spheroidal portion and along its cross-sectional configuration.
Figure 16:
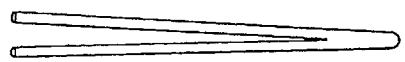
FIG. 16 is a schematic view of a V-shaped smart hollow fiber in accordance with this invention.
Figure 17:
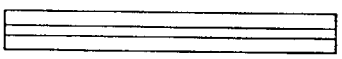
FIG. 17 is a schematic view of a double lumen smart fiber tubing in accordance with this invention.
Figure 18:
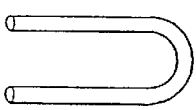
FIG. 18 is a U-shaped smart fiber tubing in accordance with this invention.
Figure 19:
FIG. 19 is a schematic view of an alternate smart fiber configuration including an A-shaped tapering enlarged area along the length thereof.
Figure 20:
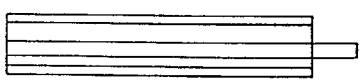
FIG. 20 illustrates a coaxial concentric assembly of a polypropylene inner hollow fiber surrounded by an outer brittle glass fiber in accordance with a preferred embodiment.
Figure 22A:
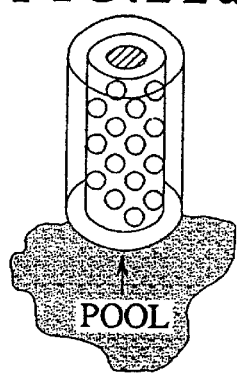
FIGS. 22a–22d are schematic views illustrating the use of specialty piezoelectric smart repair fibers to provide selective release and repair of ionically charged ion modifying agents in response to compressive loading.
Figure 22B:
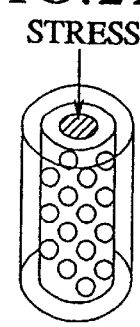
Figure 22C:
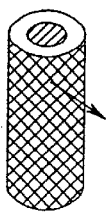
Figure 22D:
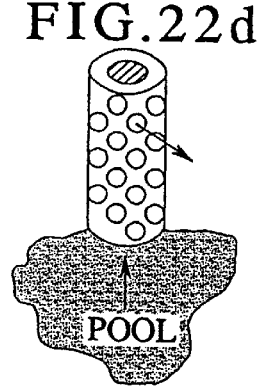

In FIGS. 13b and 13f the permeability of the matrix may be controlled by setting up a polymerized polymer within the matrix as shown in FIG. 13f to prevent permeability. This may be effected in several ways, and in one preferred embodiment, polymerizable components are freely mixed within the concrete which require only the exposure to a liquid catalyst to cause them to set up into an impermeable barrier. FIGS. 13c and 13g illustrate the release of antifreeze materials in FIG. 13g to prevent freeze/thaw and to brittleness and cracking due to ice crystals formation within the matrix from occurring. Finally, FIGS. 13d and 13h illustrate the development of local microcracks due to local loading which may be locally repaired by release of repairing adhesives as in FIG. 13h to fill cracks or voids and rebond fibers and matrices adjacent microcracks to prevent major microscopic failures from occurring.

In accordance with this invention, the smart fiber hollow fibers used to make the smart fiber reinforcements in accordance with this invention may have any desired configuration. As illustrated in FIGS. 14 through 20, a wide variety of cross-sectional configurations may be employed, as well as multi-lumen tubes and multiple concentric tube assemblies may be employed.

Figure 21:
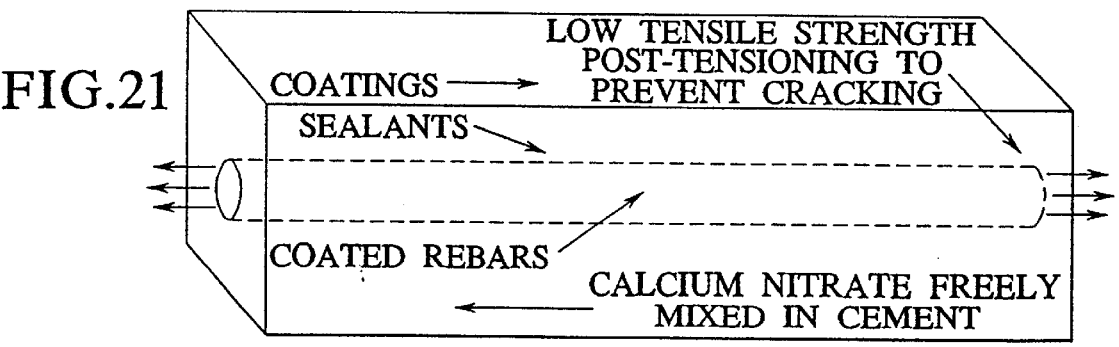
FIG. 21 is a schematic view of a new and improved anticorrosion composite matrix in accordance with this invention, illustrating the use of redundant protective features to provide an enhanced anticorrosion reinforced concrete member.

Referring now to FIG. 21, the new and improved smart fiber matrix composite materials in accordance with this invention may be used in connection with other matrix protecting practices to provide redundant protection against environmental damage. As depicted in FIG. 21, a cementitious matrix including rebars may include surface coatings and sealants to prevent the ingress of harmful environmental liquids. Calcium nitrite anticorrosion chemicals may be freely mixed within the cement and the smart fiber reinforcements may be disposed immediately adjacent the rebar containing additional anticorrosive modifying agents in accordance with this invention for release as needed when the concentration of corrosion chemicals get sufficiently high to stimulate their release.

Referring now to FIGS. 22a through 22d, there is depicted a special embodiment of the present invention wherein the notion of smart fiber release and repair is coupled with specialty fibers. As depicted in FIG. 22a through 22d, the smart fiber itself comprises a piezoelectric fiber into which a liquid chemical is first applied or deposited by providing an electric current to the piezoelectric components of the fiber. The modifying chemicals accretes within and on the surfaces of the web of fibers making up the solid piezoelectric cylinders, which in turn hollow fibers which may be placed and disposed within the matrix. In accordance with these embodiments the modifying agents are released from the piezoelectric fibers by the application of service load stresses on the matrix. These generate electrical charges in the piezoelectric fibers due to their piezoelectric character. The electrical charges cause positive ions to move from inside the porous fibers into the surrounding matrix. Negative ionic materials located in the matrix may also be drawn into or attracted to the piezoelectric hollow fiber. In this way repair can be done by dispersing charged ions into the matrix or may through by selectively drawing undesired materials into the fibers to remove them and causing damage to the matrix.

Referring now to FIGS. 23a through 23d, another specialty application for the smart fiber reinforced matrix materials in accordance with this invention is shown, which include an impermeable barrier equipped with smart sensors in addition to a hollow fiber wrapped rebar composite in accordance with this invention. The impermeable barrier may be connected to sensor equipment shown as a feedback loop capable of detecting ingress of moisture, changes in voltage or changes in chloride iron concentration.

Figure 23A:
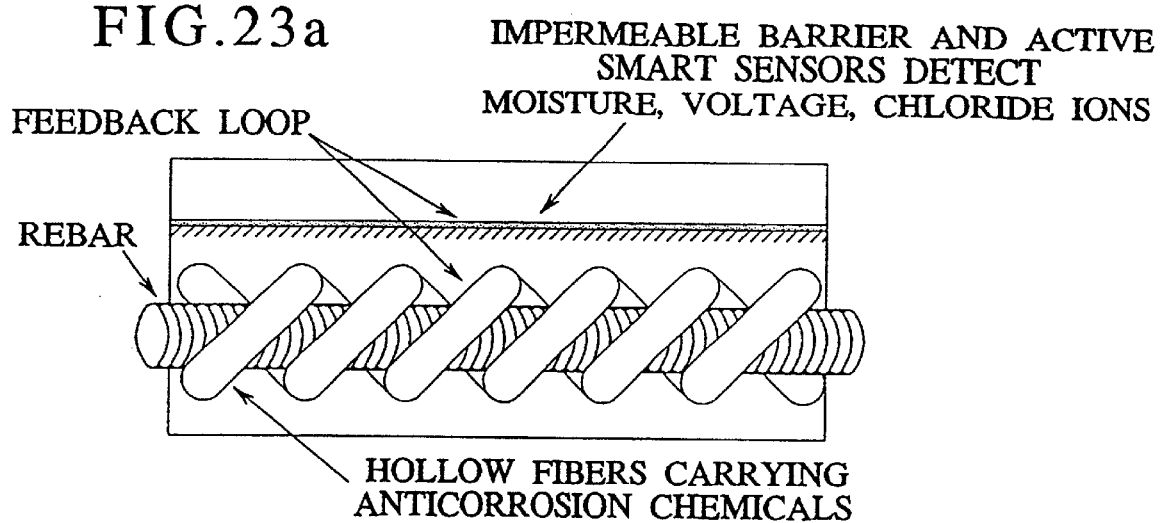
FIG. 23a is a schematic view of an alternate embodiment of a self-repairing fiber reinforced matrix composite material in accordance with this invention, illustrating the use of a smart matrix repair fiber wrapped rebar in combination with an impermeable barrier layer equipped with sensors to detect changes in moisture, voltage or chloride iron concentration within the matrix.
Figure 23B:
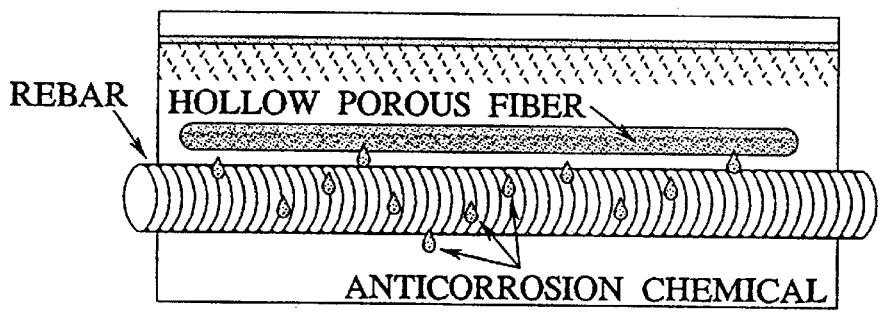
FIG. 23b is a schematic view of a preferred embodiment similar to FIG. 23a wherein the impermeable barrier is employed as an electric charge applicator to permit an applied electrical signal to cause a release of anticorrosion chemicals within the matrix adjacent, a rebar.

As shown in FIG. 23b, once the ingress of moisture is sensed at the impermeable barrier layer, an electrical signal may be sent through the inner barrier layer, causing discharge or migration of cat ions from the middle layer towards the rebar, which causes a coating on the smart fiber to be broken down to permit release of the modifying agent contained therein of anticorrosion chemicals into the immediate vicinity of the rebar to prevent corrosion.

Figure 23C:
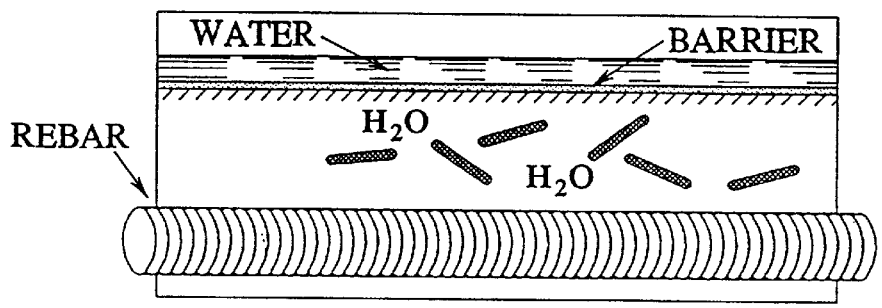

As depicted in FIGS. 23c, the hollow smart fibers in accordance with this invention are disposed in a region bounded by the barrier layer on one side and the rebar on the other to provide redundant back-up protection to the rebar to prevent corrosion. More particularly, the hollow fibers contain water binding chemicals which effectively remove the damaging water from reaching the rebar in that intermediate region, thereby preventing corrosion.

Figure 23D:
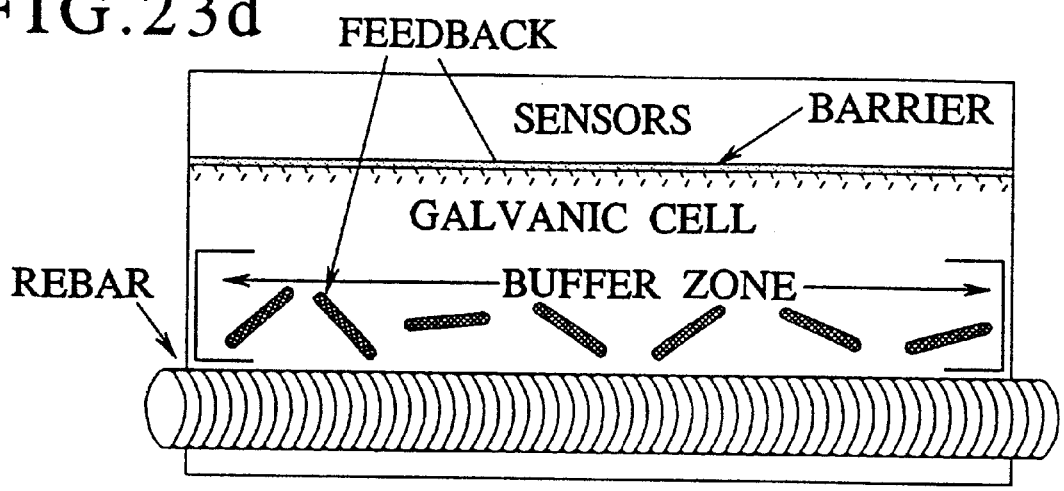
FIG. 23d illustrates a special embodiment employing a separate electrode barrier adjacent a rebar wrapped with the smart fibers which act to create a galvanic cell to release a water scavenging hydroscopic chemical when moisture intrusion is detected.
Figure 23E:
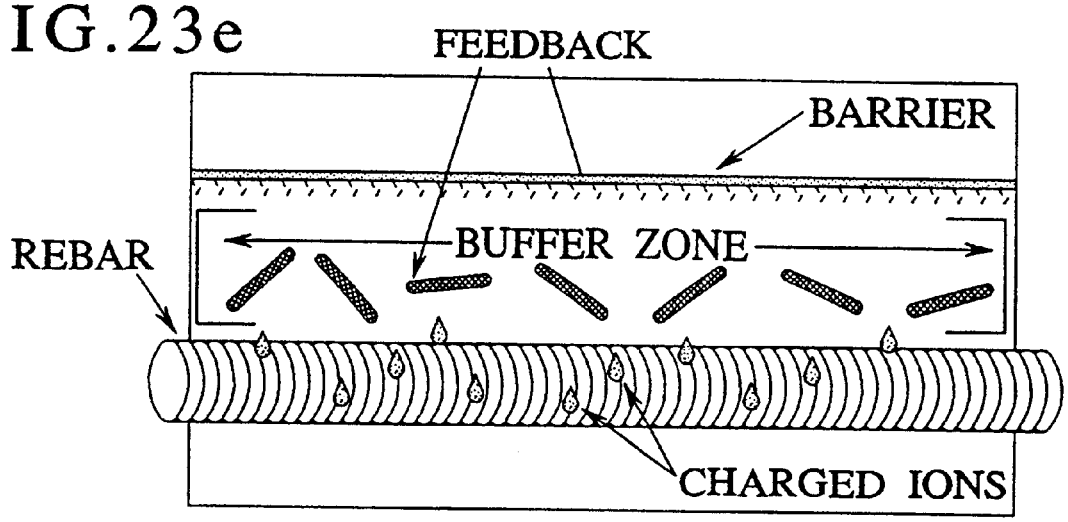
FIG. 23e is an alternate embodiment of the type shown in FIG. 23d wherein the electrode adjacent to the rebar is capable of causing smart fiber release of charged zinc ions to coat the rebar in an electroplating operation to prevent corrosion of the rebar once the ingress of water or moisture is detected.

In FIG. 23d, an alternate aspect is provided wherein the barrier is electrified to provide a galvanic cell in the immediate region between the barrier layer and the rebar. A counter galvanic cell is created about the hollow middle fibers which contain a modifying chemical inside the buffer zone, which in turn can release moisture binding hydroscopic chemicals in response to application of electrical charges or may release anticorrosive chemicals. In accordance with FIG. 23e, the hollow fibers disposed within the barrier buffer zone may include zinc ions which will migrate and coat the rebar in a galvanizing or electric lading action by application of the voltage between the barrier and rebar.

Figure 24A:
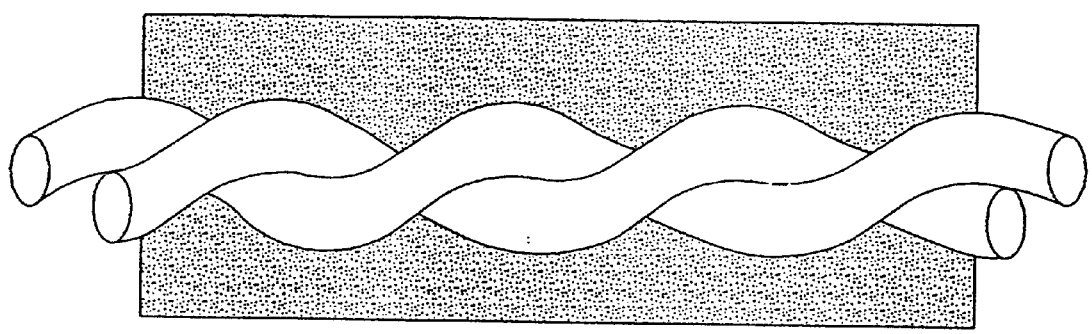
FIGS. 24a and 24b schematically illustrate an alternate embodiment of the present invention wherein the smart fibers comprise a twisted pair of fibers embedded in the matrix, as shown in FIG. 24a, and wherein changes in load on the matrix cause chemicals to be released from the twisted pair of fibers as shown in FIG. 24b and illustrating that the twisted pair of fibers may comprise optical fibers.
Figure 24B:
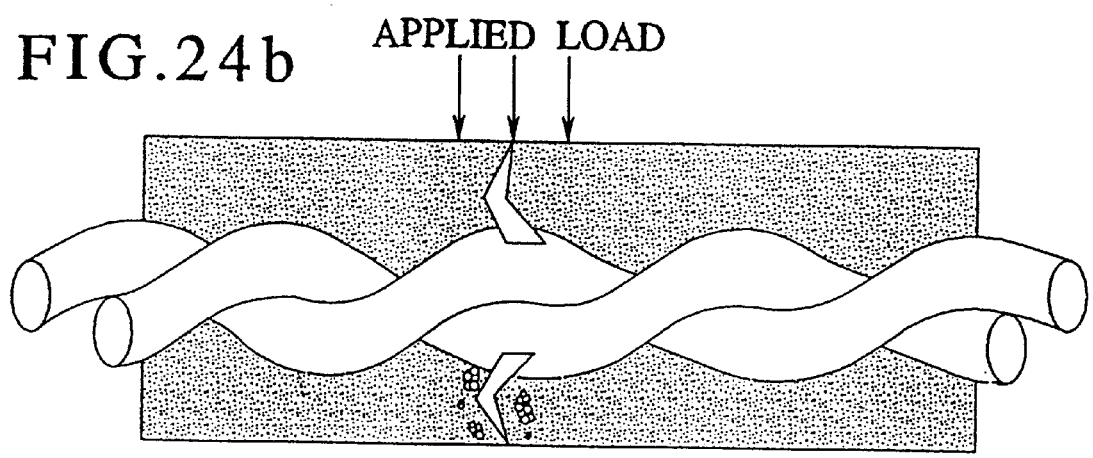

Referring now to FIGS. 24 and 24b, another specialty embodiment of the invention includes the use of optical fibers as the self-repairing fiber which in turn contains a modifying chemical which may be positioned within the matrix. Twisted pair fibers, for example, may be used as shown in FIGS. 24a and 24b. In response to the application of applied loads, the optical fibers may be changed in their transmission properties indicating a break or leak in the matrix and may in turn be caused to discharge their internal modifying agent into the surrounding matrix to, for example, repair a microcrack as shown in FIG. 24d.

Figure 25A:
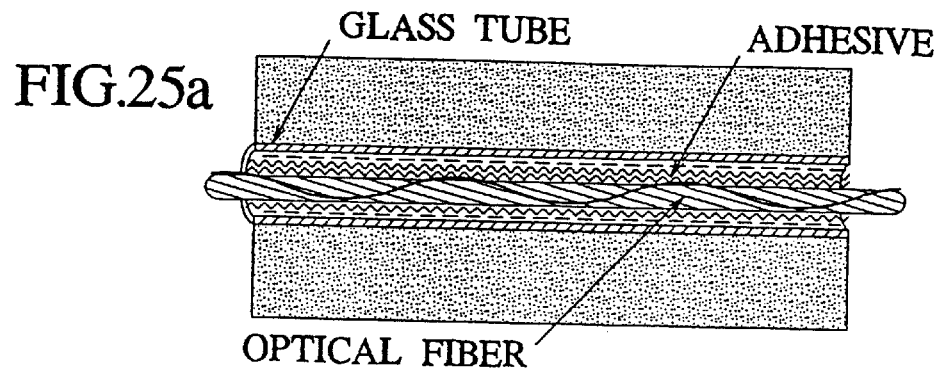
FIGS. 25a and 25b illustrate a schematic view of an alternate embodiment of a new and improved matrix in accordance with this invention, including an outer glass tube smart fiber having an optical fiber therein as well as a modifying adhesive chemical as shown in FIG. 25a and illustrating the release of adhesive due to cracking or maintaining the optical fiber in an intact condition shown in FIG. 25b.
Figure 25B:
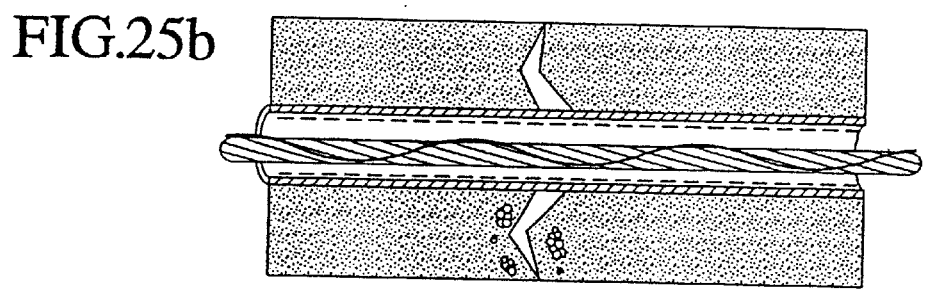

FIGS. 25a and 25b depict a similar embodiment involving the use of glass hollow fibers as surrounding hollow fibers for containing adhesive repair modifying agents and for housing an optical fiber therein. As shown in FIG. 25b, microcracking of the matrix causes release of the repair adhesive locally within the matrix to prevent further cracking and breaking which might damage the optical fiber and its transmission capability.

Figure 26A:
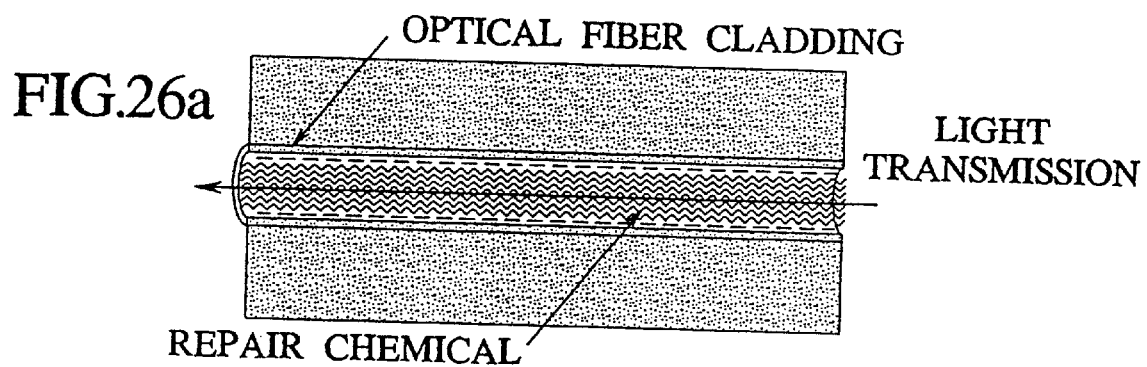
FIGS. 26a and 26b illustrate another preferred alternate embodiment of the invention, schematically illustrating an optical fiber which itself is used as the smart fiber containing repair chemical therein and having an optical fiber cladding layer along the periphery thereof as shown in FIG. 26a and showing in FIG. 26b schematically the change in light transmission properties caused by breakage of the outer glass fiber and leakage of the repair chemical to indicate that a fracture and release and repair have occurred.
Figure 26B:
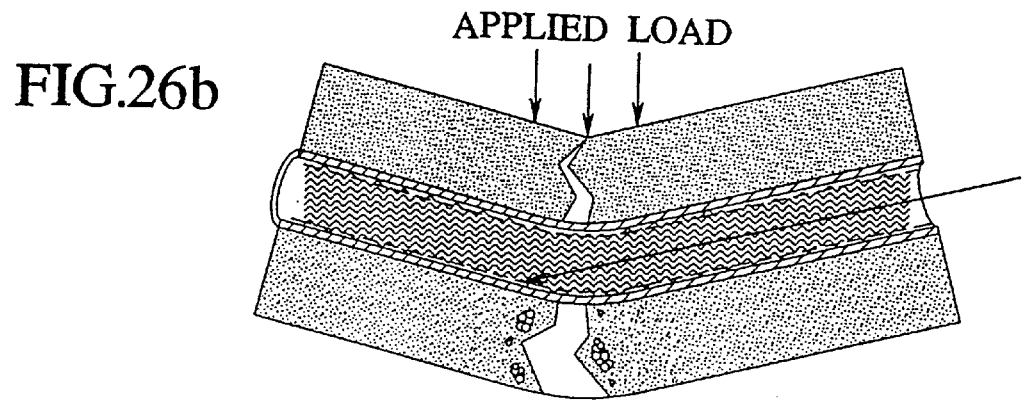

Referring now to FIGS. 26a and 26b, a different use of optical fibers as the smart fibers in a matrix composite in accordance with this invention is shown. More particularly, a cladded optical fiber having an interior cavity filled with an adhesive repair chemical is provided in a surrounding polymer or cement matrix. The light transmission of the intact fiber is of a given value. Once applied, loads are caused cracking and bending of the matrix as shown in FIG. 26b which will cause bending of the fibers decreasing the amount of light transmitted therethrough.

Figure 27A:
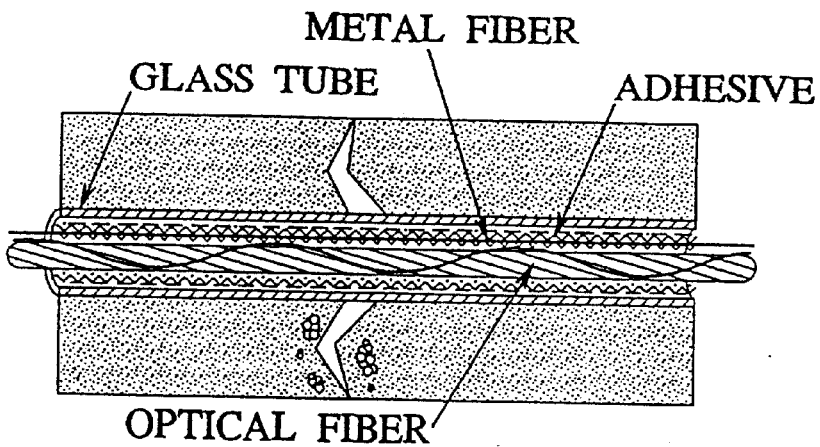
FIGS. 27a and 27b show another alternate embodiment of this invention wherein the smart repair fiber comprises an assembly of an outer glass tube and an inner metal fiber member in an optical fiber and an adhesive modifying chemical therein as shown in FIG. 27a, which in response to an applied cracking load ruptures the glass fiber to repair the crack while maintaining the optical fiber in an altered, but undamaged condition as shown in FIG. 27b.
Figure 27B:
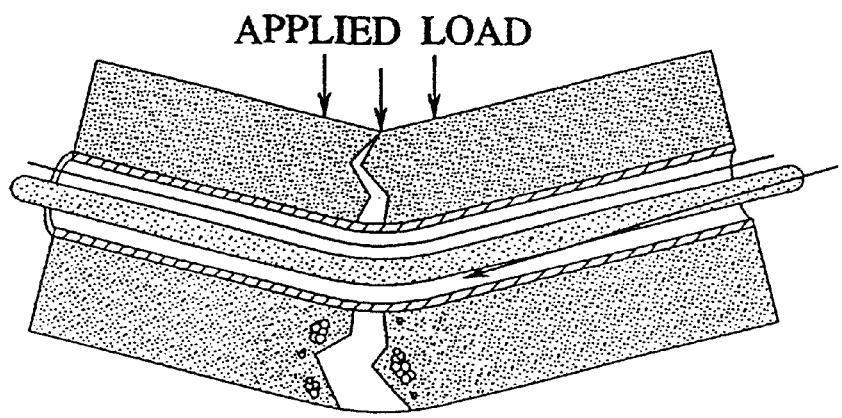

Referring now to FIGS. 27a and 27b, another glass fiber embodiment is shown wherein an assembly including an outer hollow glass tube filled with adhesive modifying agent and including an optical fiber therein and a middle fiber therein provide a special matrix composite. As shown in FIG. 27b, in response to an applied load, the middle fiber bending assist in breaking the outer glass tube to thereby release the repairing adhesive to the matrix. The optical fiber polymer may be bent or stretched and light lost to cladding coating on the fiber may be detected outside the matrix to determine bending of the fibers and possible microcracking therein.

Referring now to FIGS. 28a through 28c, another use of an optical fiber for forming the smart repair fibers in accordance with this invention illustrates reliance on release of the repair chemicals within the optical fiber to change the optical characteristics to indicate that microcracking has occurred wherein the change in volume of the repair material can indicate the volume cracks that needed to be filled and the change in refracturing index of light transmitted through the fiber may also give an indication of the volume of the cracks that have been filled in accordance with this invention.

Figure 29A:
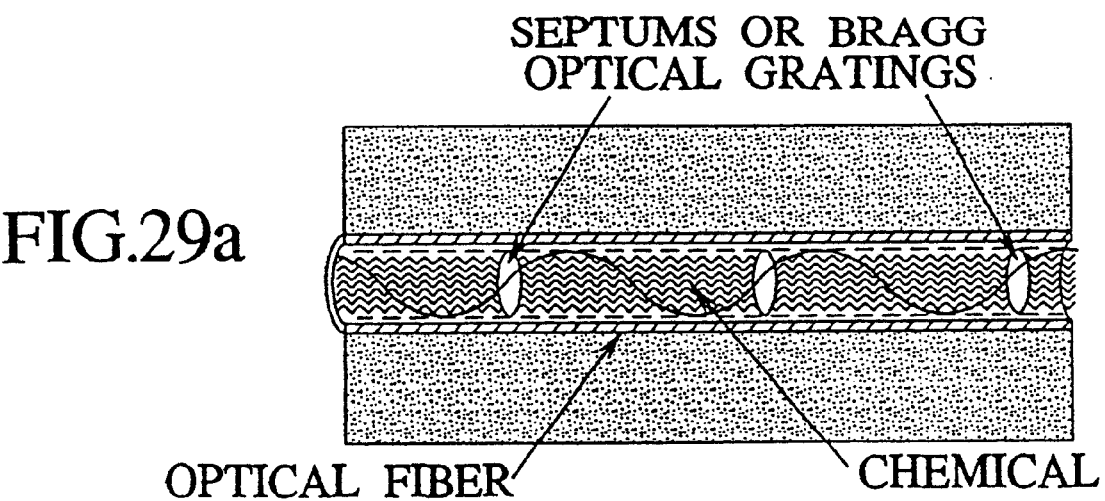
FIGS. 29a and 29b illustrate an alternate aspect of this preferred embodiment wherein septums or Brag optical gradings may be positioned at desired locations along the length of the smart repair optical fiber as shown in FIG. 29a, which may aid in indicating the location of cracks along the length of the fiber within the matrix as shown in FIG. 29b.
Figure 29B:
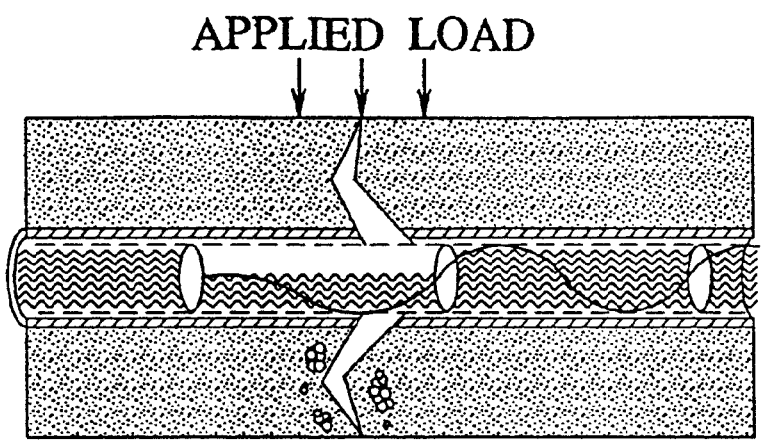

Referring now to FIGS. 29a and 29b, a plurality of septums or brag optical gradings may be positioned along the modifying agent filled optical fiber in accordance with this invention to permit the diagnostic detection of the location of cracks by noticing changes in the refracturing index located between gradings. FIGS. 29a and 29b illustrate a further preferred embodiment employing optical fibers as the hollow fiber component of the smart matrix materials in accordance with this invention. The elongate optical fiber is subdivided into longitudinal segments by dividers or septums over brag optical gradings which maintain the optical transmission characteristics along the fiber when filled with the chemical modifying agents. As depicted in FIG. 29b, in the event of a breakage and leaking of the repair chemical into the adjacent matrix, the dividers or septums limit the quantity of fluid loss to a local segment only. The change in optical characteristics in that local segment will still serve to identify the location of the crack, while preventing an overall loss in all of the fiber fluid contents.

Referring to FIGS. 30a–30d, still another optical fiber hollow fiber embodiment of this invention is depicted employing fibers of predetermined longitudinal length or dimension having a mirror end well at one end thereof and having repair chemical disposed therein. Checks on the integrity of the optical fiber segment can be made by intermittently sending an optical pulse along the short length of the fiber and bouncing it off the mirror and comparing the reflected intensity to the transmitted intensity to determine whether or not there has been a change along the length of the fiber. By placing a mirror intermediate the length of a row of fiber, the fiber sensing the optical sensing test could be performed from either end and in that manner the location of the break on one side of the mirror or the other could be determined.

Referring now to FIG. 30c, the new and improved smart matrix material is shown in a rebonded condition wherein the interior modifying agent, in this case an adhesive, has leached into the surrounding matrix to repair crack, to bond the matrix to itself, and to bond the coating to the matrix and the coating to the fiber. This restores the overall integrity of the composite, and in some cases, may lead to actual increases in overall strength and performance for the rebond material.

FIG. 30d illustrates the exterior refilling design in accordance with the preferred embodiment for vacuum pump refilling of a broken optical fiber to repair or restore optical transmission service therealong.

In accordance with the present invention, other embodiments for using the self-repairing fiber reinforcement smart matrix composite matrix materials described herein will be readily apparent to those skilled in this art. For example, employing ceramic matrices such as a hydroxyapatite ceramic minerals and reinforcing hollow fibers containing bio-compatible crack repairing adhesives may be used in joint replacements or as shaped articles for prosthetic devices. In this manner, biomedical embodiments for the smart matrix composite materials possessing the self-repair properties may be used to provide improved or extended fuselage to prosthetic devices and bone replacements. Stress load fractures occurring within the artificial bone or joint segment will self-repair in accordance with the principles of this invention.

In still another embodiment of the present invention, the overall matrices may be used in building applications to provide some seismic resistance or earthquake-proof properties to the structures. More particularly, the response of a solid matrix material containing rigid-filled fibers or liquid-filled fibers may vary in response to seismic waves. Reological fluids and electroreological fluids are known which are stiff in one condition, and thereafter upon application of electrical current, may become fluid or liquid. These fillings within reinforcing fibers may be intentionally changed periods of seismic activity in response to, for example, a sensor switch to liquefy or fluidize building structures to better withstand seismic vibration activity without causing brittleness. In the liquefied electroreological state, the overall matrix composite may be better able to withstand energy vibration than might be encountered in the solid rigid composite structure.

In still another aspect of the invention, it is known that alkali reactions are sometimes caused within cementitious matrix materials when aggregate reacts with matrix causes an expansion of the aggregate against the matrix. This causes internal stresses to develop within the matrix composite or shaped article, which usually appears as cracks within the matrix. The use of the smart fibers in accordance with the present invention containing adhesives will repair some of these cracks. In addition, instead of adhesives these smart fibers may be filled with pH modification agents such as acidic agents to neutralize the alkali reaction. In addition, fibers filled with the alkali reaction inhibiting acidic modifying agent may be used in combination with the matrix repair adhesive filled smart fibers in accordance with this invention.

In accordance with this invention, the matrix selected may vary, for example, RIBTEC mats of stainless steel fibers may be slurry infiltrated with cement, hollow fibers for repair may be included. Under loading, the mat causes the cement to form microcracks, which in accordance with this invention releases the repair adhesives into the matrix to provide a repaired high toughness composite material. Depending on the matrix selected, different fiber properties may be desired, for example, in rigid matrix materials such as cementitious set materials or sintrex ceramic materials more flexible fibers may be desirable, whereas in polymer matrices having inherent elasticity or flexibility, more rigid fibers such as glass or metal fibers may be desired. In addition, it may be desired to use fibers which become brittle over time. Fibers may be connected to each other with flexible parts to ensure that they do not break prematurely during mixing or compounding. Furthermore, chemicals which survive the long periods of time and which survive repeated temperature variations may also be used as the modifying agents. Although several different matrix materials have been disclosed or suggested herein, others may still be used by those skilled in this art. Although a number of different kinds of fibers have also been described, still other fibers might also be used by those skilled in this art in accordance with the principles of this invention. Different modifying agents and different mechanisms for selective release of the modifying agent in response to an external stimuli or internal stresses caused by other external occurrences might also be developed and designed by those skilled in the art given the principles provided herein. Accordingly, all such obvious modifications may be made herein without departing from the scope and spirit of the present invention as defined by the appended claims.

I claim as my invention:

1. A shaped article comprising:
   a shaped matrix material having at least one release vessel disposed therein, said release vessel having a releasable modifying agent contained therein and maintaining the modifying agent within the release vessel until released and releasing the modifying agent from the release vessel in the matrix material in response to at least one external stimulus.

2. A shaped article as defined in claim 1, wherein said matrix material is organic.

3. A shaped article as defined in claim 1, wherein said matrix material is inorganic.

4. A shaped article as defined in claim 1, wherein said matrix material is polymeric.

5. A shaped article as defined in claim 1, wherein said matrix material comprises an inorganic polymeric material.

6. A shaped article as defined in claim 1, wherein said matrix material comprises an organic polymeric material.

7. A shaped article as defined in claim 1, wherein said matrix material is cured.

8. A shaped article as defined in claim 1, wherein said matrix material is curable.

9. A shaped article as defined in claim 1, wherein said release vessel is organic.

10. A shaped article as defined in claim 1, wherein said release vessel is inorganic.

11. A shaped article as defined in claim 1, wherein said release vessel comprises a hollow fiber.

12. A shaped article as defined in claim 1, wherein said release vessel comprises an organic polymer.

13. A shaped article as defined in claim 1, wherein said release vessel comprises glass.

14. A shaped article as defined in claim 1, wherein said modifying agent is liquid.

15. A shaped article as defined in claim 1, wherein said modifying agent is solid.

16. A shaped article as defined in claim 1, wherein said matrix material comprises a thermoplastic polymer.

17. A shaped article as defined in claim 1, wherein said matrix material comprises a thermosettable polymer.

18. A shaped article as defined in claim 1, wherein said matrix material comprises a cross-linked polymer material.

19. A shaped article as defined in claim 1, wherein the matrix material is elastomeric.

20. A shaped article as defined in claim 1, wherein said matrix material is a construction material.

21. A shaped article as defined in claim 1, wherein said matrix material is a cementitious material.

22. A shaped article as defined in claim 1, wherein the matrix material is a cement.

23. A shaped article as defined in claim 1, wherein the matrix material comprises concrete.

24. A shaped article as defined in claim 1, wherein the matrix material comprises ceramic.

25. A shaped article as defined in claim 1, wherein the matrix material comprises metal.

26. A shaped article as defined in claim 1, wherein the matrix material is selected from carbide, oxide or hydroxy appetite materials.

27. A shaped article as defined in claim 1, wherein the matrix material comprises a metal selected from the group consisting of aluminum, iron, lead, copper, steel, bronze, phosphor bronze, and brass.

28. A shaped article as defined in claim 1, wherein said release vessel comprises a synthetic organic fiber, inorganic fiber or natural organic fiber.

29. A shaped article as defined in claim 1, wherein said modifying agent comprises an impregnator.

30. A shaped article as defined in claim 1, wherein said modifying agent comprises a sealant.

31. A shaped article as defined in claim 1, wherein said modifying agent comprises adhesive.

32. A shaped article as defined in claim 1, wherein said modifying agent comprises a water barrier.

33. A shaped article as defined in claim 1, wherein said modifying agent comprises an anti-corrosion agent.

34. A shaped article as defined in claim 1, wherein said modifying agent comprises an antifreeze agent.

35. A shaped article as defined in claim 11, wherein said modifying agent comprises a fiber protection modifying agent.

36. A shaped article as defined in claim 1, wherein said release vessel comprises a porous material having a coating, said coating being responsive to the applied external stimulus so that the coating is altered to permit the release vessel to again become porous to permit the modifying agent to be released from the release vessel.

37. A shaped article as defined in claim 1, wherein the modifying agent comprises a dye material.

38. A shaped article as defined in claim 1, wherein the modifying agent comprises a rheological or electro-rheological fluid.

39. A shaped article as defined in claim 11, wherein said release vessel comprises a plurality of modifying agent filled hollow fibers.

40. A shaped article as defined in claim 1, wherein said release vessel comprises a plurality of modifying agent filled hollow fibers disposed in a web arrangement.

41. A shaped article as defined in claim 1, wherein the release vessel is a hollow fiber comprising a shape memory alloy material.

42. A shaped article as defined in claim 1, wherein the release vessel is a hollow fiber comprising a magnetostrictive material.

43. A shaped article as defined in claim 1, wherein the release vessel comprises an electrostrictive hollow fiber.

44. A shaped article as defined in claim 1, wherein the release vessel comprises a first portion disposed in the matrix material and a second portion extending outside the matrix material.

45. A shaped article as defined in claim 1, wherein said modifying agent comprises a repair chemical for repairing micro cracks in the matrix material.

46. A shaped article as defined in claim 1, wherein said modifying agent comprises a solvent for the matrix material.

47. A shaped article as defined in claim 1, wherein the modifying agent comprises a curable composition.

48. A shaped article as defined in claim 1, wherein the modifying agent comprises an adhesive.

49. A shaped article as defined in claim 11, wherein the modifying agent after release is capable of repairing micro cracks in the matrix and re-bonding damage to interfaces between the release vessel and the matrix caused by the external stimulus.

50. An additive for providing self repairing capabilities and improving final cure properties of a shapeable matrix composition, said additive comprising:
a release vessel having a modifying agent releasably maintained therein and permitting release of the modifying agent from the release vessel into a matrix material in which the release vessel has been added in response to at least one external stimulus.

51. An additive as defined in claim 50, wherein the modifying agent is released from the release vessel into the matrix when the external stimulus acts upon the shapeable matrix composition.

52. A shaped article comprising:
a shaped article including an organic polymer matrix material having at lease one release vessel disposed therein, the release vessel releasably maintaining a modifying agent therein until the shaped article is acted upon by an external stimulus, whereupon, in response to the external stimulus, the modifying agent may be released from the release vessel into the matrix material to cause a structural change in the shaped article.

53. A shaped article comprising:
a body comprising a continuous phase and a discontinuous phase disposed in the continuous phase, the discontinuous phase comprising at least one release vessel releasably maintaining a modifying agent therein and releasing the modifying agent into the continuous phase in response to an external stimulus.

54. A shaped article as defined in claim 1, wherein the matrix material comprises an organic polymer material and the release vessel comprises a particle.

55. A shaped article as defined in claim 1, wherein the release vessel comprises a piezoelectric material.

56. A shaped article as defined in claim 1, wherein the release vessel comprises a particle.

57. A shaped article as defined in claim 36, wherein the release vessel comprises a particle.

58. A shaped article as defined in claim 1, comprising at least one optical fiber.

59. A shaped article as defined in claim 1, further comprising at least one unfilled hollow fiber having a first portion disposed in the matrix and a second portion extending outside the matrix.

60. A shaped article as defined in claim 1, further comprising voids in the matrix material.

61. A shaped article comprising:
a shaped article including a polymer matrix material having at least one hollow fiber disposed therein, the hollow fiber having a releasable modifying agent contained therein and maintaining the modifying agent within the hollow fiber until released and releasing the modifying agent from the hollow fiber into the matrix material in response to at least one external stimulus.

62. A shaped article as defined in claim 61, wherein said modifying agent, upon release, is effective to cause a structural change in the shaped article after the external stimulus has occurred.

63. A shaped article as defined in claim 61, wherein said polymer matrix material is organic.

64. A shaped article as defined in claim 61, wherein said polymer matrix material is thermoplastic.

65. A shaped article as defined in claim 61, wherein the polymer matrix material is thermosettable.

66. A shaped article as defined in claim 61, wherein the polymer matrix material is elastomeric.

67. A shaped article as defined in claim 61, wherein said hollow fiber is organic.

68. A shaped article as defined in claim 61, wherein said hollow fiber is inorganic.

69. A shaped article as defined in claim 61, wherein said hollow fiber is piezoelectric.

70. A shaped article as defined in claim 61, wherein said hollow fiber is an optical fiber.

71. A shaped article as defined in claim 61, wherein said shaped article further comprises at least one optical fiber disposed in said matrix material.

72. A shaped article as defined in claim 61, wherein said shaped article further comprises at least one unfilled hollow fiber having a first portion disposed in said matrix and a second portion extending outside the matrix.

73. A shaped article as defined in claim 61, wherein said modifying agent comprises a repair chemical for repairing micro and macro cracks in the matrix.

74. A shaped article as defined in claim 61, wherein said modifying agent is selected from the group consisting of solvents for the matrix, curable compositions and adhesives.

75. A shaped article as defined in claim 61, comprising a plurality of hollow fibers arranged in a regular array in said matrix.

76. A shaped article as defined in claim 61, wherein the modifying agent is effective upon release to repair micro and macro cracks in the matrix and re-bond damaged interfaces between the fibers and the matrix caused by the external stimulus.

77. A method for making a self-repairing shaped article comprising the steps of:

providing a shapeable polymer matrix material;

providing at least one release vessel having a releasable modifying agent contained therein and maintaining the modifying agent within the release vessel until released and releasing the modifying agent from the release vessel into a polymer matrix material to which the release vessel has been added in response to at least one external stimulus;

admixing the shapeable polymer matrix material and the at least one release vessel to form a shapeable mixture; and thereafter shaping the shapeable mixture to form a shaped article in which modifying agent may be released from the release vessel in response to an external stimulus.

78. A shaped article comprising:

a cured matrix material having a plurality of hollow fibers dispersed therein, said hollow fibers having a releasable modifying agent contained therein and maintaining the modifying agent within the fibers until released and permitting release of the modifying agent into the matrix material in response to at least one external stimulus.

79. A shaped article as defined in claim 78, wherein said matrix material is a settable construction material.

80. A shaped article as defined in claim 78, wherein said matrix material is a cementitious material.

81. A shaped article as defined in claim 78, wherein said hollow fibers comprise polypropylene, polyamide, glass, ceramic or cellulose.

82. A shaped article as defined in claim 78, wherein said hollow fibers are elastomeric.

83. A shaped article as defined in claim 78, wherein said hollow fibers are porous polypropylene.

84. A shaped article as defined in claim 78, wherein said modifying agent is a liquid.

85. A shaped article as defined in claim 78, wherein said modifying agent comprises an impregnator, a sealant, an adhesive, a water barrier, an anti-corrosion agent, an anti-freeze agent or a fiber protection agent.

86. A shaped article as defined in claim 78, wherein the hollow fiber comprises a coating material disposed on the hollow fiber.

87. A shaped article as defined in claim 86, wherein said coating maintains the modifying agent within the hollow fiber.

88. A shaped article as defined in claim 78, wherein the modifying agent filled hollow fibers comprise less than about 10 volume percent of said matrix material.

89. A shaped article as defined in claim 78, wherein said matrix material is an inorganic matrix material.

90. A method for making a shaped article comprising the steps of:

preparing a curable matrix material in an uncured state;

adding to the uncured matrix material at least one hollow fiber having a releasable modifying agent contained therein to provide a filled hollow fiber containing matrix material and shaping and curing the filled hollow fiber containing matrix material to provide a shaped article in which the modifying agent may be released from the at least one hollow fiber in response to an external stimulus.

91. An additive for improving final cured properties of a curable matrix composition, said additive comprising:

a hollow fiber having a releasable modifying agent contained therein and maintaining the modifying agent within the fiber until released and permitting release of the modifying agent into a matrix material in which the hollow fiber has been added in response to at least one external stimulus.

92. An additive as defined in claim 91, wherein the hollow fiber comprises polypropylene, polyamide, glass, ceramic or cellulose.

93. An additive as defined in claim 91, wherein said at least one hollow fiber comprises a porous material.

94. An additive as defined in claim 91, wherein the modifying agent is a liquid.

95. An additive as defined in claim 91, wherein the hollow fiber comprises a coating on the hollow fiber.

96. An additive as defined in claim 91, wherein said modifying agent comprises an impregnator, a sealant, an adhesive, a water barrier, an anti-corrosion agent, an anti-freeze agent or a fiber protection agent.

97. An additive as defined in claim 91, wherein the hollow fiber comprises glass.

98. A shaped article comprising:

a shaped matrix material having at least one hollow fiber disposed therein, said hollow fiber having a releasable modifying agent contained therein and maintaining the modifying agent within the fiber until released and releasing the modifying agent from the fiber into the matrix material in response to at least one external stimulus.

99. A shaped article as defined in claim 98, wherein said matrix material is a construction material.

100. A shaped article as defined in claim 98, wherein said matrix material is a cementitious material.

101. A shaped article as defined in claim 98, wherein said hollow fiber comprises polypropylene, polyamide, ceramic, glass or cellulose.

102. A shaped article as defined in claim 98, wherein the hollow fiber is elastomeric.

103. A shaped article as defined in claim 98, wherein the hollow fiber comprises porous polypropylene.

104. A shaped article as defined in claim 98, wherein the modifying agent is a liquid.

105. A shaped article as defined in claim 98, wherein said modifying agent comprises an impregnator, a sealant, an adhesive, a water barrier, an anti-corrosion agent, an anti-freeze agent or a fiber protection modifying agent.

106. A shaped article as defined in claim 98, wherein the hollow fiber comprises a coating disposed on the fiber.

107. A shaped article as defined in claim 98, including a plurality of modifying agent filled hollow fibers present in an amount of less than about 10 volume % of said matrix material.

108. A shaped article as defined in claim 98, wherein said matrix material is inorganic.

109. A shaped article as defined in claim 98, wherein said at least one hollow fiber is organic.

110. A shaped article as defined in claim 98, wherein the hollow fiber is inorganic.

111. A shaped article as defined in claim 98, wherein the modifying agent is a solid.

112. A shaped article as defined in claim 108, wherein said inorganic matrix material is selected from cement, concrete, ceramic or metal matrix materials.

113. A shaped article as defined in claim 112, wherein said ceramic matrix material is selected from carbide, oxide or hydroxy apatite materials.

114. A shaped article as defined in claim 112, wherein said metal matrix material comprises aluminum, iron, led, copper, steel, bronze, phosphor bronze or brass.

115. A shaped article as defined in claim 98, wherein said hollow fiber comprises glass.

116. A shaped article as defined in claim 98, wherein the hollow fiber comprises an optical fiber.

117. A shaped article as defined in claim 98, wherein said hollow fiber comprises a piezoelectric fiber.

118. A shaped article as defined in claim 106, wherein said coating comprises a chemically sensitive coating, an electrically sensitive coating or a radiation sensitive coating.

119. A shaped article as defined in claim 118, wherein said coating is a chemically sensitive coating selected from moisture sensitive coatings, pH sensitive coatings, ion sensitive coatings or solvent sensitive coatings.

120. A shaped article as defined in claim 118, wherein said coating comprises an electrically sensitive coating selected from current sensitive coatings or voltage sensitive coatings.

121. A shaped article as defined in claim 118, wherein said coating comprises a radiation sensitive coating selected from light sensitive coatings, temperature sensitive coatings, or radioactivity sensitive coatings.

122. A shaped article as defined in claim 98, wherein said modifying agent comprises a dye material.

123. A shaped article as defined in claim 98, wherein said article is a containment structure for radioactive or chemical waste materials.

124. A shaped article as defined in claim 98, comprising at least one optical fiber disposed in the matrix.

125. A shaped article as defined in claim 98, comprising a plurality of modifying agent filled hollow fibers disposed in a web arrangement within the matrix.

126. A shaped article as defined in claim 98, wherein said at least one hollow fiber comprises a shaped memory alloy material.

127. A shaped article as defined in claim 98, wherein said at least one hollow fiber comprises a magnetostrictive material.

128. A shaped article as defined in claim 98, wherein the at least one hollow fiber comprises an electrostrictive material.

129. A shaped article as defined in claim 1, wherein the external stimulus comprises laser excitation.

130. A shaped article as defined in claim 1, wherein the external stimulus comprises an external force applied to the shaped article.

131. A shaped article as defined in claim 1, further comprising at least one other fiber which responds to a stimulus in a manner which is effective to squeeze modifying agent out of a release vessel.

132. A shaped article as defined in claim 131, wherein the other fiber comprises shape memory alloy or a piezoelectric material.

133. A shaped article as defined in claim 131, wherein the other fiber is selected from fibers which change their shape in response to applied light, an applied magnetic field, an applied electric field, an applied voltage, an applied current or a change in the chemical environment.

134. A shaped article as defined in claim 1, wherein the shaped article comprises a covering disposed on a surface.

135. A shaped article as defined in claim 131, wherein the other fiber provides for sensing the shaped article.

136. A shaped article as defined in claim 1, comprising a plurality of release vessels including release vessels including release vessels containing different modifying agents.

137. A shaped article as defined in claim 1, wherein said shaped article comprises a body component for aircraft, spacecraft, automobile, or structural parts.

138. A shaped article as defined in claim 1, wherein said shaped article comprises a molded part.

139. A shaped article as defined in claim 1, wherein said modifying agent comprises a repair chemical for repairing surface cracks in the matrix.

140. A shaped article as defined in claim 1, further comprising one or more other release vessels adapted for sensing a condition of the matrix, for reconfiguring the matrix or for repairing the matrix.

141. A shaped article as defined in claim 1, comprising release vessels disposed within other release vessels.

142. A shaped article as defined in claim 141, wherein the release vessels within other release vessels include fibers within fibers.

143. A shaped article as defined in claim 1, further comprising at least one other release vessel containing a signal material.

144. A shaped article as defined in claim 1, wherein the release vessels may be reused after release has occurred to permit internal sensing or administration of other agents in the matrix.

* * * * *